(12) United States Patent
Zhang et al.

(10) Patent No.: US 9,200,067 B2
(45) Date of Patent: Dec. 1, 2015

(54) MOLECULAR MARKER CUEDC2 PROTEIN FOR PROGNOSTIC DETERMINATION OF BREAST CANCER ENDOCRINOLOGY THERAPY

(75) Inventors: Xuemin Zhang, Beijing (CN); Tao Zhou, Beijing (CN); Xin Pan, Beijing (CN); Huiyan Li, Beijing (CN); Ailing Li, Beijing (CN)

(73) Assignee: Biomedical Analysis Center of Academy of Military Medical Sciences, Beijing (CN)

( * ) Notice: Subject to any disclaimer, the term of this patent is extended or adjusted under 35 U.S.C. 154(b) by 0 days.

(21) Appl. No.: 13/981,271

(22) PCT Filed: Oct. 28, 2011

(86) PCT No.: PCT/CN2011/081479
§ 371 (c)(1),
(2), (4) Date: Aug. 23, 2013

(87) PCT Pub. No.: WO2012/100573
PCT Pub. Date: Aug. 2, 2012

(65) Prior Publication Data
US 2014/0066604 A1    Mar. 6, 2014

(30) Foreign Application Priority Data
Jan. 24, 2011   (CN) .......................... 2011 1 0024862

(51) Int. Cl.
G01N 33/53    (2006.01)
C07K 16/18    (2006.01)
C07K 16/30    (2006.01)

(52) U.S. Cl.
CPC ............ *C07K 16/18* (2013.01); *C07K 16/3015* (2013.01)

(58) Field of Classification Search
None
See application file for complete search history.

(56) References Cited

U.S. PATENT DOCUMENTS

2006/0188889 A1* 8/2006 Burgess et al. ................... 435/6

OTHER PUBLICATIONS

Hy et al (Nat Immunol, 2008, 9(5): 533-541).*
Li et al (Nature Immunology, 2007, 9(5): 533-541).*
Zhang et al (EMBO J, 2007, 26(7): 1831-1842).*
Ren et al (Cancer Letters, 2008, 264: 83-92).*
Monoclonal Antibody Production (A report of the Committee on Methods of Producing Monoclonal Antibodies), Institute for Laboratory Animal Research, National Research Council, National Academy Press, 1999.*
Brodeur et al (J Immunol Methods, 1986, 86(2): Abstract).*
Yu et al (Journal of Xi'an Jiaotong University, 2009, 30(3): 269-271).*
Turashvili et al (BMC Cancer, 2007, 7(55): 1-20).*
Dressman et al (Clin Cancer Res, 2006, 12(3): 819-826).*

* cited by examiner

*Primary Examiner* — Sean Aeder
(74) *Attorney, Agent, or Firm* — SHEPPARD MULLIN RICHTER & HAMPTON LLP

(57) ABSTRACT

Disclosed is a use of the CUEDC2 protein in the preparation of diagnostic agents for prognostic determination of the endocrinology therapy for the breast cancer patients and for the diagnosis of tumor such as breast cancer and ovarian cancer. The diagnostic agent comprises an antibody against the CUEDC2 protein, wherein the antibody is a monoclonal or polyclonal antibody against the CUEDC2 protein. Provided is a kit or a composition for prognostic determination of endocrinology therapy for the breast cancer patients and for the diagnosis of tumors such as breast cancer and ovarian cancer. The kit or composition comprises an antibody against the CUEDC2 protein. Further disclosed is a use of the CUEDC2 gene or protein in preparation of drugs for treating tumors, that is, small molecular substances and specific antibodies that specifically inhibit the expression or activity of the CUEDC2 gene\protein are used as a therapeutic agent to restore the sensitivity of drug-resistant tumors to drug treatment. The new use of the CUEDC2 protein provides a new basis for determining a dosage regimen of adjuvant therapy after surgical operation of the breast cancer patients, thereby improving the therapeutic effect of the anti-cancer drugs and alleviating the suffering and economic burden of the patients.

2 Claims, 24 Drawing Sheets

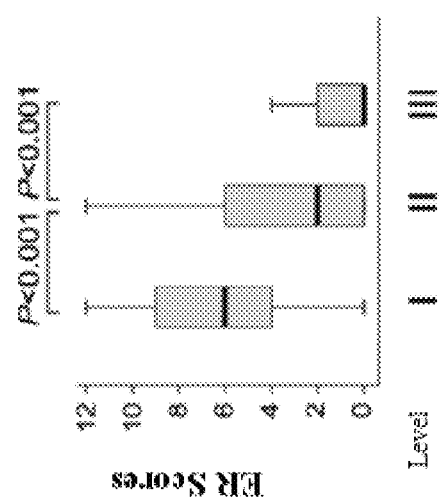
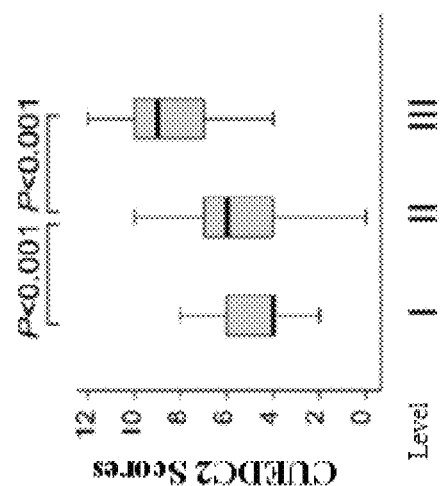
Figure 9b
Figure 9a

```
SEQUENCE LISTING

<160> NUMBER OF SEQ ID NOS: 4

<210> SEQ ID NO 1
<211> LENGTH: 25
<212> TYPE: RNA
<213> ORGANISM: Homo sapiens

<400> SEQUENCE: 1
ccaagaugag gcaacuggcg cugag                                        25

<210> SEQ ID NO 2
<211> LENGTH: 25
<212> TYPE: RNA
<213> ORGANISM: Homo sapiens

<400> SEQUENCE: 2
ccuaugugcc uggcuucgcc cacau                                        25

<210> SEQ ID NO 3
<211> LENGTH: 25
<212> TYPE: RNA
<213> ORGANISM: Homo sapiens

<400> SEQUENCE: 3
ccgaccucag uggcuuggau gaggu                                        25

<210> SEQ ID NO 4
<211> LENGTH: 25
<212> TYPE: RNA
<213> ORGANISM: Homo sapiens

<400> SEQUENCE: 4
ggauuucgag ucgucuuaau guaua                                        25
```

MOLECULAR MARKER CUEDC2 PROTEIN FOR PROGNOSTIC DETERMINATION OF BREAST CANCER ENDOCRINOLOGY THERAPY

CROSS-REFERENCE TO RELATED APPLICATIONS

This application is a National Phase application under 35 U.S.C. §371 of PCT Application PCT/CN2011/081479, filed Oct. 28, 2011, which claims the benefit of Chinese Application No. CN201110024862.4, filed Jan. 24, 2011, which applications are hereby incorporated by reference in their entirety.

TECHNICAL FIELD

The present invention relates to a new use of the CUEDC2 protein, and more particularly, to a new use of the CUEDC2 protein in the preparation of a diagnostic agent for prognostic determination of endocrinology therapy for breast cancer patients, to a new use of the CUEDC2 gene or protein in the preparation of a drug for treating tumors, and to a kit and a composition for prognostic determination of endocrinology therapy for breast cancer patients. The present invention also relates to a use of the CUEDC2 protein in a diagnostic agent, a kit and a composition for diagnosis of tumors such as breast cancer, ovarian cancer and so on.

BACKGROUND ART

As tumors are serious diseases that threaten human health, the study of tumor-related genes has always been an important subject of human biology. Breast cancer is a common tumor, which is one of the most malignant tumors for women, and it usually occurs in European and American countries. In China, especially in some developed areas, the incidence of breast cancer rises year by year, and breast cancer has been a serious threat for women's health.

Estrogen receptor α (ERα) is a hormone-dependent nuclear transcription factor; it is expressed in about 70% of breast tumors. The estrogen binds to estrogen receptor, inducing receptor dimerization, and then the receptor is recruited to the estrogen response element in ERα target gene promoter regions. Since ERα plays a major role in the development and progression of breast cancer, the current endocrine therapy of breast cancer is mainly target ERα signaling pathways, including: reducing estrogen levels; antagonizing ERα function; or decreasing ERα expression levels. In these target ERα endocrine therapies, tamoxifen, a selective estrogen receptor modulator, can bind to ERα through competition and suppress the growth of breast cancer, and it has become the predominant endocrine therapy of breast cancer in recent 30 years. However, primary or secondary tamoxifen resistances are important challenges for the treatment of this disease. ERα itself is the most important determinant to determine whether or not breast cancer is sensitive to the endocrine therapy, and the decrease or elimination of ERα expression level often causes resistance to endocrine therapy. Studies have shown that, the decrease of ERα expression level usually is due to post-transcriptional or post-translational regulation in certain breast cancer tumors. For example, Src and AIB 1 can decrease ERα level in hormone dependent manner; however the mechanism of the decrease of ERα level in breast cancer is not fully clear.

CUEDC2 (Gene ID: 79004) is a protein whose function is not clear. Bioinformatics analysis indicates that CUEDC2 contains a CUE domain. It has been reported that CUE domain is a kind of relatively conservative ubiquitin-binding domain and it contains about 40 amino acids. It widely exists in many eukaryotic proteins. CUE domain can bind to ubiquitin monomer and polyubiquitin. Our previous study found that CUEDC2 degrades the progesterone receptor and participates in the breast cancer cell growth regulation (Zhang, P. J., Zhao, J., et al. 2007. CUE domain containing 2 regulates degradation of progesterone receptor through ubiquitin-proteasome. EMBO J 26(7): 1831-1842). Our recent study shows that CUEDC2 binds to IKK complex, recruits GADD34 and PP1, suppresses over-activation of NF-κB signaling pathway, and involves in the regulation of inflammatory response (Li, H. Y., Liu, H., et al. 2008. Deactivation of the kinase IKK by CUEDC2 through recruitment of the phosphatase PP1. Nat Immunol 9(5): 533-541).

SUMMARY OF THE INVENTION

An object of the present invention is to provide a use of the CUEDC2 protein in the preparation of a diagnostic agent for prognostic determination of the endocrinology therapy for the breast cancer patients, a use of the CUEDC2 protein in the preparation of a diagnostic agent for diagnosis of tumors and a use of the CUEDC2 gene or protein in the preparation of drugs for treating tumors.

A further object of the present invention is to provide a kit and a composition for prognostic determination of endocrinology therapy for the breast cancer patients.

A further object of the present invention is to provide a kit and a composition for diagnosis of tumors.

The CUEDC2 protein in the present invention refers to CUE domain containing 2 proteins, GenBank: BAE19942.1, publication date is Aug. $19^{th}$, 2005.

The objects of the present invention are achieved by the following research findings:

1. CUEDC2 can down regulate ERα level through ubiquitin proteasome pathway.

In breast cancer MCF-7 cells, over expression of CUEDC2 causes endogenous ERα protein level decreased in a hormone independent manner (FIG. 1). In MCF-7 and ZR-75-1 cells, ERα expression level is increased by CUEDC2 siRNA transfected (FIG. 2). Furthermore, in MCF-7 cells, over expression of CUEDC2 can elevate ubiquitination level of ERα, while knocking down the expression of CUEDC2 with specific siRNA can reduce ubiquitination level of ERα (FIG. 3). The luciferase reporter assay using estrogen receptor specific reporter genes (FIG. 4) and the reverse transcription PCR experiment (FIG. 5) show that CUEDC2 can reduce the transcriptional activity of ERα and the transcription of its target genes.

2. The expression level of CUEDC2 is elevated in breast cancer tissue

In order to study the expression level of CUEDC2 in breast cancer tissue, first of all, CUEDC2 monoclonal antibody was prepared as follows: first, the CUEDC2 full-length coding sequence was constructed into pGEX-KG prokaryotic expression vector. The GST-CUEDC2 fusion expression vector was transformed into *E. coli* DH5α, IPTG was added to induce expression and GST-CUEDC2 fusion protein was purified. Then, 100 μg GST-hCUEDC2 fusion protein was sufficiently emulsified with Freund's complete adjuvant, with which to subcutaneously inject for the first time to BAL B/c female mice aged between 4 to 6 weeks. 3 weeks after the first immunization, 100 μg GST-hCUEDC2 fusion protein was sufficiently emulsified with Freund's incomplete adjuvant, with which to subcutaneously inject for the second time to the BAL B/c mice. On the 15th day after the third immunization, blood was drawn via the tail vein and the serum antibody titer was measured by ELISA. 3 days after booster-immunization, spleen cells were extracted and fused with SP2/0 cells of mouse myeloma cell line by conventional methods, screened by indirect ELISA method and cloned by limiting dilution. Specifically, cell suspension was diluted, and seeded in 96-well plates, so as to make only one cell seeded in each well in theory to produce monoclone and thereby hybridoma cells that secrete completely homogeneous monoclonal antibody were obtained. The resulting hybridoma cells were injected intraperitoneally to the BAL B/c mice. About 12 days later, ascites were collected and mAb-ascites were obtained. The purified mAb was prepared by AbMaX Biotechnology Co., Ltd.

Using the CUEDC2 antibody prepared above, the inventors carried out an immunohistochemical analysis for 449 breast cancer cases. Results showed that, the expression of CUEDC2 in breast tumor tissues was significantly higher than that in matched adjacent normal tissues (FIG. 6, $P<0.001$). The results of real-time quantitative PCR of 16 cases showed that, the expression of CUEDC2 mRNA in tumor tissues of breast cancer was also increased significantly.

3. Inverse correlation of CUEDC2 with ERα in breast cancer

The inventors further performed immunohistochemical analysis for important molecular markers, such as ER, PR, Ki-67, HER-1 and HER-2, in the 449 breast cancer cases, and scored the staining results. Then the inventors performed relative analysis about the scores of the above molecular markers and CUEDC2, and the results showed that CUEDC2 expression negatively correlated with ERα and PR expression and positively correlated with expression of Ki-67 and HER-2 expression, whereas no statistical correlation between CUEDC2 expression level and HER-1 expression level, the details are listed in Table 1 below.

TABLE 1

The Correlation Analysis of CUEDC2 expression with other Breast Cancer markers.

| Name | Cases (n) | Correlation with CUEDC2 | P Value |
|---|---|---|---|
| ERα | 449 | −0.259 | 2.71E−08 |
| PR | 449 | −0.182 | 1.07E−04 |
| Ki-76 | 426 | 0.405 | 2.75E−18 |
| EGFR (HER-1) | 447 | 0.058 | 0.22 |
| ERBB2 (HER-2) | 449 | 0.305 | 3.90E−11 |

A further analysis about the expression levels of CUEDC2, ERα and PR in breast cancer patients showed that patients having higher CUEDC2 expression levels had lower expression levels and lower positive rates of ERα and PR (FIG. 8). Among different histological grades of breast cancer patients, the higher the histological grades, the higher the CUEDC2 expression levels, at the same time, the higher the tumor grades, the lower the ERα expression levels (FIG. 9a and FIG. 9b). The above results showed that CUEDC2 expression has an inverse correlation with ER-α in breast cancers.

4. Breast cancer patients with higher CUEDC2 expression level were less sensitive to tamoxifen therapy.

The inventors performed a survival analysis to 228 breast cancer patients with follow-up data. 115 of the patients received tamoxifen therapy, and for these 115 patients, both disease-free survival and overall survival of patients with higher CUEDC2 expression levels were lower than those of patients with lower CUEDC2 expression levels (FIG. 10a and FIG. 10b). While the other 113 patients did not receive tamoxifen therapy, and for these 113 patients, no matter CUEDC2 expression level is higher or lower, neither disease-free survival nor overall survival had any statistical differences (FIG. 11a and FIG. 11b). The results above showed that CUEDC2 was likely to be the clinical determinant for resistance of breast cancer patients to tamoxifen and even other endocrine drugs such as estrogen receptor antagonists (such as tamoxifen and ICI-1827), aromatase inhibitors (such as anastrozole and letrozole) and LH-RH agonists (such as zoladex and goserelin).

5. Over expression of CUEDC2 in breast cancer cells can reduce the sensitivity of the cells to tamoxifen.

MCF-7 cells stably transfected with CUEDC2 were treated with different doses of tamoxifen, and then the cell growth was assayed. The results showed that, over expression of CUEDC2 really caused MCF-7 cells insensitive to tamoxifen. Furthermore, if the over expression of CUEDC2 in MCF-7 cells was knocked down by CUEDC siRNA, the sensitivity of cells to tamoxifen can be restored (FIG. 12). In addition, clony-formation assays showed that, over expression of CUEDC2 noticeably made cells insensitive to tamoxifen-induced cell death (FIG. 13). In order to verify the above conclusion, the inventors further conducted animal experiments. MCF-7 cells stably expressing CUEDC2 were injected into the mammary fat pad of ovariectomized nude mice, and tamoxifen sustained-release tablets were embedded subcutaneously in neck, and then the tumor growth was observed. The results showed that, compared with the control group, tamoxifen could significantly inhibit the growth of MCF-7 cells in nude mice, but could not effectively inhibit the tumor growth in nude mice with MCF-7 cells over expressing CUEDC2 (FIG. 14).

The inventors' research showed that as a new molecular marker, CUEDC2 protein can be used in the preparation of diagnostic agents for prognostic determination of the endocrinology therapy for breast cancer patients, especially in the judgment of tamoxifen resistance.

6. CUEDC2 differentially expressed in kidney tumor tissues and non-neoplastic tissues.

As shown in FIG. 15b, tissue microarrays were stained with CUEDC2 specific antibody, and the sample size of the two groups were both n=39. There were significant differences in statistical analysis, $P<0.01$, t test.

7. CUEDC2 differentially expressed in different grades of glioma tissues.

As shown in FIG. 16b, tissue microarrays were stained with CUEDC2 specific antibody, and the sample sizes of the two groups for statistical analysis were n=23 and n=45. There were significant differences in statistical analysis, $P<0.01$, t test.

8. CUEDC2 differentially expressed in para-carcinoma tissues and prostate carcinoma tissues.

As shown in FIG. 17, tissue microarrays were stained with CUEDC2 specific antibody, and the sample sizes of the two groups for statistical analysis were n=15 and n=72. There were significant differences in statistical analysis, $P<0.01$, t test.

9. CUEDC2 differentially expressed in normal tissues and endometrial adenocarcinoma tissues.

As shown in FIG. 18, tissue microarrays were stained with CUEDC2 specific antibody, and the sample sizes of the two groups for statistical analysis were n=20 and n=60. There were significant differences in statistical analysis, $P<0.01$, t test.

10. CUEDC2 differentially expressed in benign ovarian tumor tissues and ovarian cancer tissues.

As shown in FIG. 19(a), tissue microarrays were stained with CUEDC2 specific antibody, the left image shows the benign ovarian tumor tissue and the right image shows the ovarian cancer tissue. The scale was 50 μm.

FIG. 19(b) is a boxplot graph, which shows the differential expressions of CUEDC2 protein in benign ovarian tumor tissues and ovarian cancer tissues. Tissue microarrays were stained with CUEDC2 specific antibody, and the sample sizes of the two groups for statistical analysis were n=16 and n=54. There were significant differences in statistical analysis, $P<0.01$, t test.

In conclusion, the analysis on CUEDC2 expression in different tumor tissues showed that the CUEDC2 expression levels in tissues of breast cancer, kidney cancer, ovarian cancer, glioma, prostate cancer and endometrial carcinoma were significantly higher than in normal tissues.

SUMMARY OF THE INVENTION

The present invention provides a use of the CUEDC2 protein in the preparation of diagnostic agents for prognostic determination of endocrinology therapy for breast cancer patients, wherein said diagnostic agents comprise an antibody against the CUEDC2 protein.

Preferably, said antibody is a monoclonal antibody or polyclonal antibody of said CUEDC2 proteins.

Preferably, endocrine drugs for the endocrinology therapy comprise estrogen receptor antagonists, aromatase inhibitors, LH-RH agonists; said estrogen receptor antagonists comprise tamoxifen and ICI82780; said aromatase inhibitors comprise anastrozole and letrozole; said LH-RH agonists comprise zoladex and goserelin.

The present invention further provides a kit for prognostic determination of endocrinology therapy for the breast cancer patients, wherein said kit comprises an antibody against the CUEDC2 protein.

Preferably, said antibody is a monoclonal antibody or polyclonal antibody of said CUEDC2 proteins.

Preferably, endocrine drugs for the endocrinology therapy comprise estrogen receptor antagonists, aromatase inhibitors, LH-RH agonists; said estrogen receptor antagonists comprise tamoxifen and ICI82780; said aromatase inhibitors comprise anastrozole and letrozole; said LH-RH agonists comprise zoladex and goserelin.

Preferably, said kit further contains 10×PBS, citrate buffer, haematin solution, TBS solution, 3% hydrogen peroxide solution, differentiation solution, blocking solution, antibody dilution solution, DAB (diamino benzidine) chromogenic agent. The above solutions are prepared as follows:

10×PBS (dilute 10-fold before use): 2 g potassium chloride (KCl), 80 g sodium chloride (NaCl), 17.8 g $Na_2HPO_4.2H_2O$, 2.4 g $KH_2PO_4$, and 800 ml distilled water.

Citrate buffer (pH 6.0): 9 ml 0.1M citric acid solution and 41 ml sodium citrate solution are added to 450 ml distilled water, the pH of the solution is 6.0.

Haematin solution: 1 g hematoxylin, 10 ml absolute alcohol, 20 g alum (aluminum potassium sulfate), 0.5 g mercuric oxide, 190 ml distilled water, and 10 ml glacial acetic acid (HOAc).

TBS solution: 12.1 g Tris(hydroxymethyl)methylaminomethane (Tris), 17.5 g sodium chloride (NaCl), 7 ml concentrated hydrochloric acid, add distilled water to 2000 ml, pH7.6.

3% hydrogen peroxide solution: add 50 ml 30% $H_2O_2$ into 4500 ml distilled water, to be used to block endogenous peroxidase.

Differentiation solution (1% HCl/70% ethanol): 1 ml concentrated hydrochloric acid, 70 ml ethanol and 29 ml distilled water.

Blocking solution: 5-10% non-immune goat serum and 90%-95% PBS solution. Usually the serum species are selected from secondary antibody animal serums.

Antibody dilution Solution: 15 mM/L sodium azide ($NaN_3$), 1% bovine serum albumin (BSA), 0.01M/L PBS pH7.4.

DAB (diamino benzidine) chromogenic agent: 50 mg DAB powder, 100 ml 0.05 mol/L TBS (0.05M, pH7.6), and 30-40 μL 30% $H_2O_2$. Preparation method: simply filter out the sediment. Firstly, dissolve DAB with a small amount of TBS, and then add in the rest of TBS, and mix the solution uniformly until the final concentration of DAB is 0.05%. After said solution is filtered, add in 30-40 μL 30% $H_2O_2$ before staining.

The present invention further provides a composition for prognostic determination of endocrinology therapy for the breast cancer patients, and said composition comprises an antibody against the CUEDC2 protein.

Preferably, said antibody is a monoclonal antibody or polyclonal antibody of said CUEDC2 protein.

Preferably, endocrine drugs for the endocrinology therapy comprise estrogen receptor antagonists, aromatase inhibitors, LH-RH agonists; said estrogen receptor antagonists comprise tamoxifen and ICI182780; said aromatase inhibitors comprise anastrozole and letrozole; said LH-RH agonists comprise zoladex and goserelin.

The present invention further provides a use of the CUEDC2 gene or protein in the preparation of drugs for treating tumors; said drugs comprise specific small molecules and antibodies which can inhibit the expression or activity of the CUEDC2 gene or protein. CUEDC2 protein is highly expressed in said tumors.

Preferably, said drugs comprise siRNA or shRNA, which can bind to CUEDC2 mRNA and knockdown the expression of said CUEDC2 mRNA, or comprise specific small molecules and antibodies which can inhibit the expression or activity of the CUEDC2 gene or protein.

The present invention further provides a use of CUEDC2 protein in the preparation of diagnostic agents for diagnosis of tumors. Said diagnostic agents comprise said an antibody against the CUEDC2 protein.

Preferably, the antibody is a monoclonal antibody or polyclonal antibody of said CUEDC2 protein. Said tumors comprise breast cancer, kidney cancer, ovarian cancer, glioma, prostate cancer and endometrial carcinoma.

The present invention further provides a kit for diagnosis of tumors, and said kit comprises an antibody against the CUEDC2 protein.

Preferably, the antibody is a monoclonal antibody or polyclonal antibody of said CUEDC2 protein. Said tumors comprise breast cancer, kidney cancer, ovarian cancer, glioma, prostate cancer and endometrial carcinoma.

Preferably, said kit further comprises 10×PBS, citrate buffer, haematin solution, TBS solution, 3% hydrogen peroxide solution, differentiation solution, blocking solution, antibody dilution solution, DAB (diamino benzidine) chromogenic agent. The preparation methods for said solutions are the same as those for the solutions in the kit used for prognostic determination of endocrinology therapy for the breast cancer patients.

The present invention further provides a composition for diagnosis of tumors, and said composition comprises an antibody against the CUEDC2 protein.

Preferably, the antibody is a monoclonal antibody or polyclonal antibody of said CUEDC2 protein. Said tumors comprise breast cancer, kidney cancer, ovarian cancer, glioma, prostate cancer and endometrial carcinoma.

The prognosis effect of treating breast cancer with endocrine drugs is evaluated in steps as follows:

a) Detect the expression levels of CUEDC2 protein in biological specimens obtained from breast cancer patients.

b) Analyze the detection results of step a), and score said biological specimens. The scoring standard is based on the widely accepted semi-quantitative method, which takes into account both staining intensity and staining range at the same time (wherein the staining method is immune staining). According to staining intensity and staining range, the final score of each said biological sample is a weighted product of staining intensity and staining range, wherein said staining intensity is represented as follows: none=0, weak=1, medium=2, strong=3, and said staining range is represented as follows: 0%=0, 1-24%=1, 25-49%=2, 50-74%=3, 75-100%=4, and the final score range is 0-12.

Wherein, said CUEDC2 protein expression levels are divided into following three levels: low (0-4), medium (5-8), high (9-12), wherein the low CUEDC2 protein expression level refers to that the score is in the range of 0-4, the medium CUEDC2 protein expression level refers to that the score is in the range of 5-8, and the high CUEDC2 protein expression level refers to that the score is in the range of 9-12. The high CUEDC2 expression level indicates that the prognosis of treating breast cancer with the endocrine drug is not good; and the low or medium CUEDC2 expression level indicates that the prognosis of treating breast cancer with the endocrine drug is good. It should be known to the skilled in the field that the score ranged 0-12, and the three levels (low, medium and high) of scoring standard are used in the present invention for illustration only. According to the thoughts of the present invention, the skilled in the field can recognize to use different score ranges and different score standards to assess the CUEDC2 protein expression levels in tumor tissues.

According to the present invention, the use of the CUEDC2 protein to prepare the diagnostic agents for prognostic determination of the endocrinology therapy for breast cancer patients, that is, the use of the CUEDC2 protein as the molecular marker of prognostic determination of the endocrinology therapy for breast cancer patients, has the following advantages: the effect of endocrine therapy largely depends on the expression level of ERα which is the major targeting estrogen receptor of endocrinology therapy for breast cancer patients. Although about 70% of breast cancer patients have ERα expression, still 40% of these patients are insensitive to endocrinology therapy. In addition, the expression levels of PR and HER-2 are also closely related to the effect of endocrinology therapy, they have been widely used to guide clinical medication in endocrinology therapy, but a more accurate prediction of therapeutic effect depends on findings of more drug-resistance related molecules. We found that, breast cancer patients with higher CUEDC2 expression levels have relatively lower ERα expression levels and are insensitive to endocrinology therapy. Therefore, CUEDC2 can be used as a new molecular marker to predict the sensitivity of breast cancer patients to endocrinology therapy, and can be used alone or with other traditional molecular markers for prognosis determination so as to improve the accuracy and to guide clinical medication better. The CUEDC2 protein provides a new basis for determining a dosage regimen of adjuvant therapy after surgical operation of the breast cancer patients, thereby improving the therapeutic effect of the anti-cancer drugs and alleviating the suffering and economic burden of the patients. In addition, CUEDC2 can be used as a treatment site, small molecular substances and specific antibodies that specifically inhibit the expression or activity of the CUEDC2 gene\protein can be used as a therapeutic drug to restore the sensitivity of drug-resistant tumors to drug treatment.

BRIEF DESCRIPTION OF THE DRAWINGS

FIG. 6 provides graphs of expression of CUEDC2 in breast cancer tissues, describing that the expression level of CUEDC2 in breast cancer tumor tissue is significantly increased than in normal para-carcinoma tissue. Wherein.

FIG. 8 shows the correlation between the expression of CUEDC2 and those of ERα and PR, describing that breast cancer patients with higher expression levels of CUEDC2 have lower expression levels and lower positive rates of ERα and PR. Wherein, FIG. 8a shows different expression levels of ERα in breast cancer patients having different CUEDC2 expression levels; FIG. 8b shows different positive rates of ERα in breast cancer patients having different CUEDC2 expression levels; FIG. 8c shows different expression levels of PR in breast cancer patients having different CUEDC2 expression levels; FIG. 8d shows different positive rates of PR in breast cancer patients having different CUEDC2 expression levels.

FIGS. 9a and 9b show expression levels of CUEDC2 and ERα in breast cancer patients with different histological grades, describing that CUEDC2 expression levels are elevated along with the increase of tumor grades, and ERα expression levels decrease along with the increase of tumor grades.

DETAILED DESCRIPTION OF THE PREFERRED EMBODIMENTS

Figure 1:
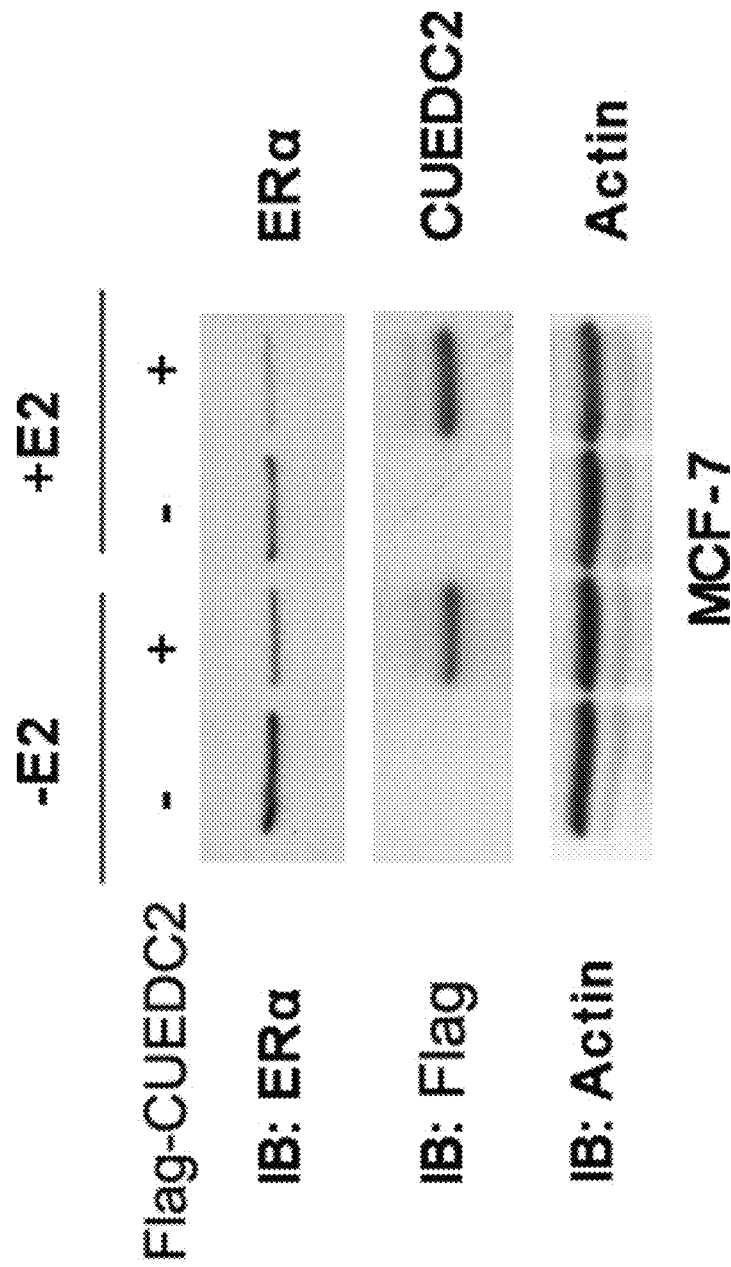
FIG. 1 shows the effect of CUEDC2 on estrogen receptor (ERα), describing that the over expression of CUEDC2 in MCF-7 cells of breast cancer causes endogenous ERα protein level decreased in a hormone-independent manner.

The present invention will be described in more details with reference to the accompanying embodiments. It should be understood that these embodiments are merely illustrative of the present invention, but the scope of the invention should not be construed to be limited by these embodiments.

Embodiment 1: Ubiquitination and Degradation of ERα by CUEDC2

I. Materials:

E. coli DH5α was purchased from Dingguo Bio Company and the catalogue No. of the product was MCC011. The estrogen was purchased from Sigma Company. The mouse monoclonal antibody anti-HA (F-7), anti-Myc (9E10) and anti-β-Actin were all purchased from Santa Cruz Biotechnology Company. The mouse antibody Flag (M2) was purchased from Sigma Company. Lipofectamine-2000 was purchased from Invitrogen Company. The MCF-7 cell was purchased from ATCC (Manassas, Va.), and its preservation no. was HTB-22, the ZR-75-1 cell was purchased from ATCC (Manassas, Va.), and its preservation no. was CRL-1500. Wherein, the MCF-7 cell was incubated in the medium, Dulbecco's Modified Eagle's Medium (DMEM), which contained 10% fetal bovine serum, 2 mML-Glutamine, antibiotics, the ZR-75-1 cell was incubated in RPMI-1640 medium, and placed in the humidity incubator with 37° C. constant temperature and 5% concentration of $CO_2$. The anti-CUEDC2 antibody was prepared by expressing and purifying GST-hCUEDC2 fusion protein in E. coli, and immunizing mice.

The CUEDC2 protein monoclonal antibody was prepared as follows: Firstly, the CUEDC2 full length coding sequence was constructed into the prokaryotic expression vector pGEX-KG. The GST-CUEDC2 fusion expression vector was transformed into E. coli DH5α, IPTG was added to induce the expression and GST-CUEDC2 fusion protein was purified. 100 µg GST-hCUEDC2 fusion protein was sufficiently emulsified with Freund's complete adjuvant, with which to subcutaneously inject for the first time to BAL B/c female mice aged between 4 to 6 weeks. 3 weeks after the first immunization, 100 µg GST-hCUEDC2 fusion protein was sufficiently emulsified with Freund's incomplete adjuvant, with which to subcutaneously inject for the second time to the BAL B/c mice. On the $15^{th}$ day after the third immunization, blood was drawn via the tail vein, the serum antibody titer was measured by ELISA. 3 days after booster-immunization, spleen cells were extracted and fused with SP2/0 cells of mouse myeloma cell line by conventional methods, screened by indirect ELISA method and cloned by limiting dilution. Specifically, cell suspension was diluted, and seeded in 96-well plates, so as to make each well had only one cell seeded in theory to produce monoclone and thereby hybridoma cells that secrete completely homogeneous monoclonal antibody was obtained. The resulting hybridoma cells were injected intraperitoneally to the BAL B/c mice. About 12 days later, ascites were collected and mAb-ascites were obtained. The purified mAb was prepared by AbMaX Biotechnology Co., Ltd.

The polyclonal antibody of CUEDC2 protein was prepared as follows: Firstly, the CUEDC2 full-length coding sequence was constructed into the prokaryotic expression vector pGEX-KG. The GST-CUEDC2 fusion expression vector was transformed into E. coli DH5α, IPTG was added to induce the expression and the GST-CUEDC2 fusion protein was purified. 100 µg GST-hCUEDC2 fusion protein was sufficiently emulsified with Freund's complete adjuvant, with which to subcutaneously inject into a rabbit around its shoulders.

In week 0, 2 ml blood was collected (0.5-1 ml preimmune serum was obtained), 200 µg antigen mixed with complete Freund's adjuvant (CFA) was used to immunize the rabbit. In week 2, 200 µg antigen mixed with complete Freund's adjuvant (CFA) was used to immunize the rabbit. In week 4, 100 µg antigen mixed with incomplete Freund's adjuvant (IFA) was used to immunize the rabbit. In week 5, 20-30 ml test serum was taken, tested by ELISA and WB using cells or tissue specimens, and 100 µg antigen dissolved in physiological saline was used to immunize the rabbit. In week 7, 20-30 ml blood was collected for the second time, and 100 µg antigen dissolved in physiological saline was used to immunize the rabbit. In week 8, 20-30 ml blood was collected for the third time, and 100 µg antigen dissolved in physiological saline was used to immunize the rabbit. In week 9, 20-30 ml blood was collected for the last time, the mixed blood specimens were purified, on average, 100-150 mg antibody could be obtained for each time of purification, and quality tests such as ELISA and WB were finally conducted.

II. The Method:

1. The Establishment of CUEDC2 Stably Expressing Cell Line.

CUEDC2 expression vector was integrated into target MCF-7 cells by retrovirus infection method as follows:

Day 1: pMSCV-IRES-GFP-Flag-CUEDC2 and helper plasmids were transfected into 293T cells by Calcium phosphate method.

Day 2: replaced with fresh culture medium after 6 h of transfection.

Day 3: seeded the target MCF-7 cells in a 6-well plate, and each well had 5×10$^5$ cells seeded.

Day 4: the virus supernatant was filtered with 45 μm filter and then added into the target MCF-7 cells seeded.

Day 6: The target cells in 6-well plate were repeatedly subcultured into a 10 cm Petri dish.

Day 10: GFP-positive cells were sorted with a flow cytometry.

After the stable cell line was obtained, test the effect of over expression by Western blot.

2. RNA Interference Experiment.

The CUEDC2 and the control siRNA were purchased from Invitrogen Company, the interference sequences were respectively listed as follows:

```
                                         (SEQ ID NO: 1)
siCUEDC2#1:
5'-CCAAGAUGAGGCAACUGGCGCUGAG-3';

(SEQ ID NO: 2)
siCUEDC2#2:
5'-CCUAUGUGCCUGGCUUCGCCCACAU-3';

(SEQ ID NO: 3)
siCUEDC2#3:
5'-CCGACCUCAGUGGCUUGGAUGAGGU-3'.

(SEQ ID NO: 4)
siControl:
5'-GGAUUUCGAGUCGUCUUAAUGUAUA-3'.
```

1.5 μg siRNA was transfected into MCF-7 cells by the transfection reagent Lipofectamine 2000, and the cells were collected for a Western-blotting test after 48 hours of transfection.

3. Ubiquitination Experiment.

The CUEDC2 protein was stably over expressed or knocked down in MCF-7 cells, 16 hours before collecting cells, 30 μM of the proteasome inhibitor, MG132 (Sigma), was added into the cells. After the processing is completed, the cells were lysed in the lysis buffer (50 mM Tris-HCl pH8.0, 150 mM NaCl, 1 mM EDTA, 0.1% NP-40 10% glycerol, 1 mM DTT, 1× cocktail). The cell lysates were immunoprecipitated with the ERα antibody, and the immunoprecipitates were collected for a Western blot test, and then tested with the ubiquitin antibody.

4. Luciferase Activity Assay.

(1) 0.2 μg ERE-TK-Luc reporter gene, 0.02 μg reporter gene pRL-TK and different doses of CUEDC2 expression plasmid were all transfected into MCF-7 cells and T47D cells. After 6 hours of transfection, changed the culture medium and added 10 nm hormone for treatment. After 24 hours of treatment, the cells were lysed, specifically, the culture medium was discarded, the cells were washed with PBS to remove the residual medium, tried to remove the remnant of PBS completely before adding in the lysis solution, then added 250 μl 1× lysis solution prepared in advance into the cultivation wells. The culture plate was placed into a shaker and shaken for 15 minutes at room temperature. Then the cell lysis solution was transferred to a centrifuge tube, and after 30 seconds of high speed centrifugation, the supernatant was transferred to a new microcentrifuge tube. Detected the luciferase activity by the following method: mixed 10 μl cell lysis solution with 50 μl Luciferase Assay Reagent II, after the solution was mixed uniformly 2-3 times with a pipettor, transferred the solution to a fluorescence spectrophotometer for detection; then took out the test tube and added in 50 μl Stop&Glo® Reagent; conducted the detection after the solution was mixed uniformly, and recorded the ratio of two results.

5. Total Cellular RNA Extraction and RT-PCR

Firstly, all appliances were soaked in diethylpyrocarbonate (DEPC) to remove RNase. Glass wares were baked at high temperature for more than 4 hours. Both the tips and the microcentrifuge tube were commercial RNase-free products. CUEDC2 was stably transfected into MCF-7 cells, treated with the estrogen for 12 hours, and then the cells were collected and repeatedly washed three times with 1× ice-cold PBS, at last all PBS was discarded and TRIZOL (Sigma) was added in. Being mixed uniformly, the solution was placed at 4° C. overnight. Then, the solution was centrifuged at 12,000 rpm for 10 minutes to remove the fat, protein and high molecular weight DNA. The centrifugal supernatant was collected and placed at room temperature for 5 minutes, and then 0.2 ml chloroform was added per 1 ml TRIZOL, and placed at room temperature for 2-3 minutes after being shocked and mixed uniformly. After the solution was centrifuged for 15 minutes at 12,000 rpm, RNA existed in the upper aqueous phase, and the upper aqueous phase was transferred into a new centrifuge tube carefully, added with 0.5 ml isopropanol and placed at room temperature for 10 minutes. Then, the solution was centrifuged for 10 minutes at 12,000 rmp, all supernatant was discarded, and the sediments were washed with 1 ml 75% ethanol. Centrifuged the solution for 5 minutes at 6,000 rmp, discarded all supernatant, and dried in air for 10 minutes. The sediments were dissolved in RNase-free water, added with 5 μl DnaseI and placed at 37° C. for 30 minutes. At last, added chloroform to more than doubled volume, and centrifuged for 5 minutes after shocking and mixing uniformly, then, the upper liquid was carefully pipetted and transferred to a new tube, and quantified with an ultraviolet spectrophotometer. The solution was subjected to 1% agarose gel electrophoresis, and ribosomal RNA bands of 5S, 18S and 28S could be seen clearly. 1 μg RNA and 1 μl oligo dT random primers (50 μmol/L) were taken, added with water to 12.5 μl, and released for 10 minutes at 70° C., then naturally cooled to room temperature. After a little centrifugation, 5 μl 5× reverse transcription buffer, 2 μl dNTP mixture (2 mmol/L), 1 μl Rnase inhibitor and 0.5 μl M-MLV reverse transcriptase (Promega) were added into the solution. The RT-RCR reaction conditions were as follows: reaction for 1 hour at 42° C., and inactivation for 15 minutes at 17° C. At last, took the reverse transcribed cDNA as the template to do RT-PCR analysis with Cyclin D1, pS2, CATD and primers of GAPDH.

Figure 2:
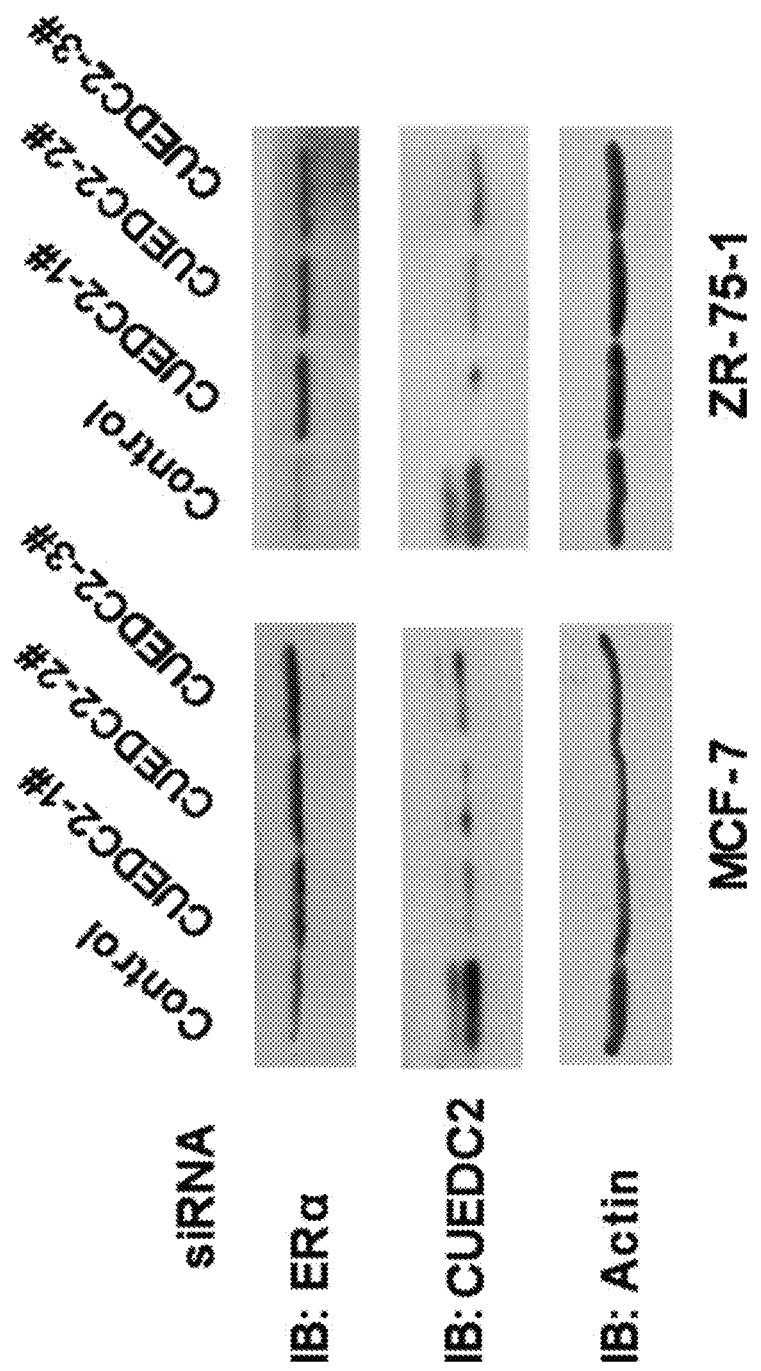
FIG. 2 shows the effect of knocking-down CUEDC2 on ERα, describing that the transfected CUEDC2 siRNA in MCF-7 and ZR-75-1 cells causes ERα expression level elevated.
Figure 3:
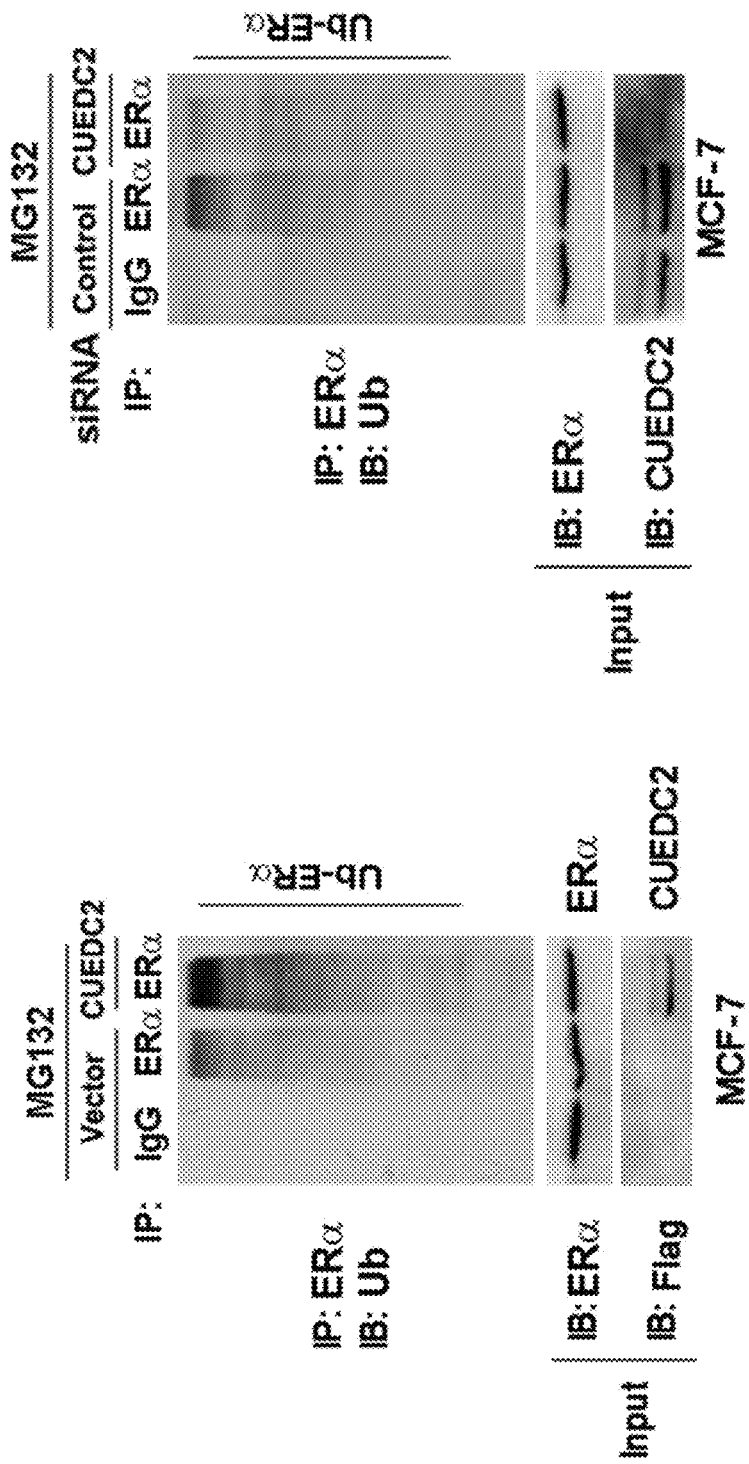
FIG. 3 shows the effect of CUEDC2 on the ubiquitination level of ERα, describing that the over expression of CUEDC2 in MCF-7 cells can elevate the ubiquitination level of ERα; while the ubiquitination level of ERα can be decreased by knocking down the expression of CUEDC2 with specific siRNA.
Figure 4:
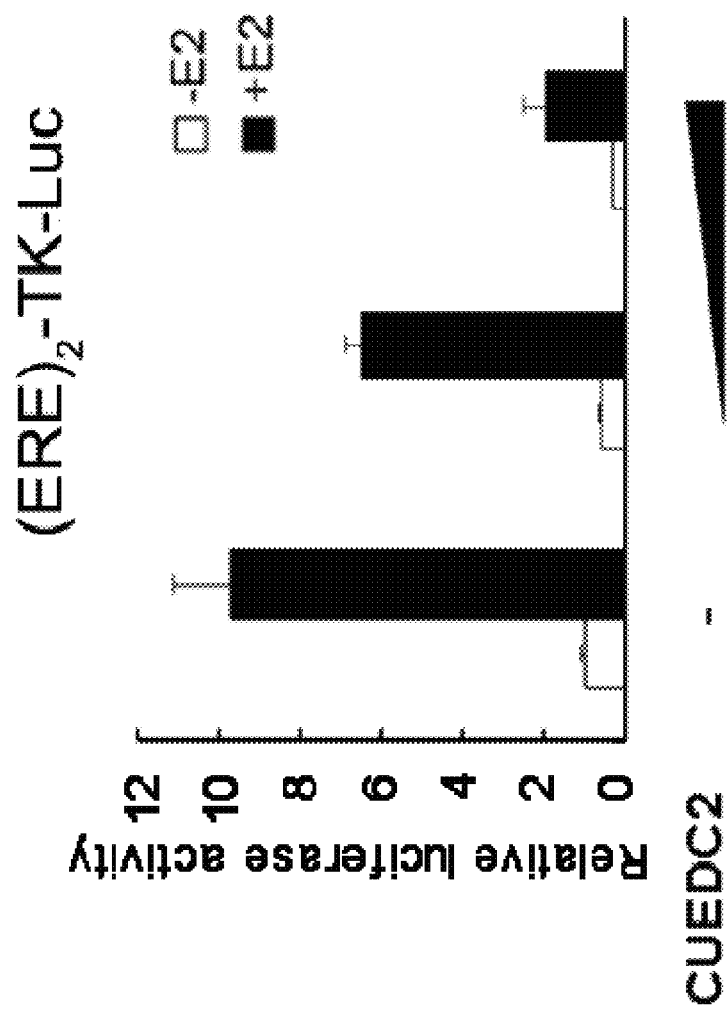
FIG. 4 shows the effect of CUEDC2 on the transcriptional activity of ERα, describing that the results of luciferase reporter assay made with estrogen receptor reporter genes.
Figure 5:
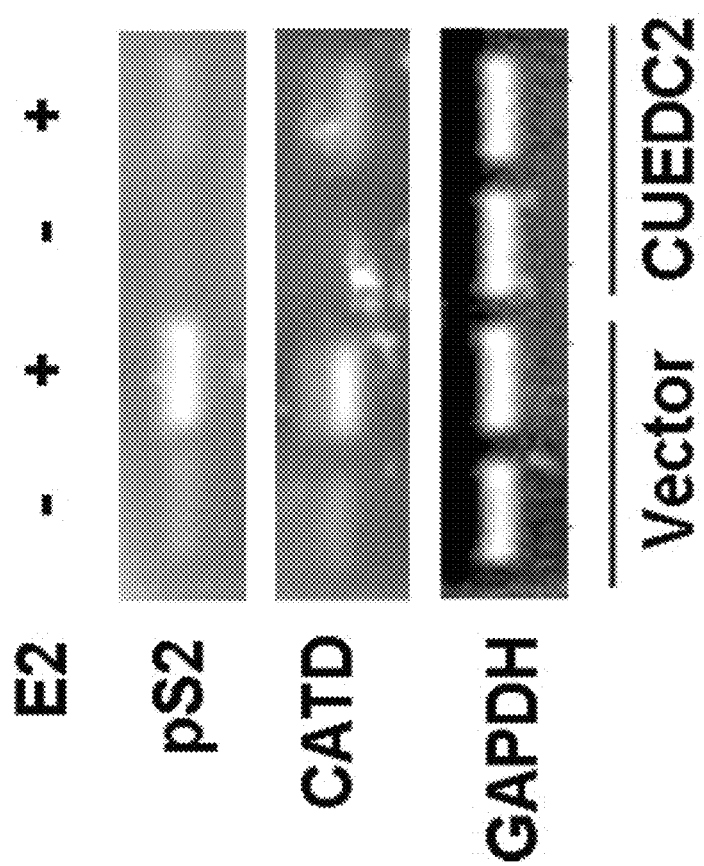
FIG. 5 is a reverse transcription PCR experiment graph, describing that the experiment results of the effect of CUEDC2 over expression on the expression of ERα target gene mRNA.

III. The Result:

In the breast cancer MCF-7 cells, the over expression of CUEDC2 causes endogenous ERα protein level decreased in a hormone independent manner (FIG. 1). In MCF-7 and ZR-75-1 cells, ERα expression level was increased by CUEDC2 siRNA transfected (FIG. 2). Furthermore, in MCF-7 cells, over expression of CUEDC2 can increase ubiquitination level of ERα, while knocking down the expression of CUEDC2 with specific siRNA can reduce ubiquitination level of ERα (FIG. 3). The luciferase reporter assay using estrogen receptor specific reporter genes (FIG. 4) and the reverse transcription PCR experiment (FIG. 5) showed that CUEDC2 can reduce the transcriptional activity of ERα and the transcription of its target genes.

Embodiment 2: High Expression Level of CUEDC2 in Breast Cancer Tumor Tissues.

I. The Material:

There were 449 cases of formalin-fixed breast cancer samples from the People's Liberation Army (PLA) General Hospital. Wherein, 228 patients were treated from 2000 to 2004, with clinical follow-up data. The other 221 patients were treated from 2006 to 2008. According to the WHO classification criteria, the cancer histological grades of the 449 cases were defined into grade 1 (72 cases), grade 2 (266 cases) and grade 3 (111 cases). The clinical stage was also defined according to the WHO classification criteria. All of tumors occurred for the first time, with detailed clinical information including immunohistochemical test results of ERα, PR, EGRF (HER-1), ERBB2 (HER-2/Neu) and Ki-67. All patients received radical mastectomy and regular lymph node dissection, and the lymph node metastasis was determined according to histological detection. The tumor size was defined as the largest diameter of tumor in surgery. The anti-CUEDC2 antibody was prepared by the method as mentioned in the embodiment. We also used tissue microarrays to detect the expression levels of CUEDC2 in ovarian tumors and para-carcinoma tissues by the immunohistochemical method.

II. The Method:

The source of tissue slices used for CUEDC2 immunohistochemical analysis, and ERα, PR, EGRF (HER-1), ERBB2 (HER-2/Neu) and Ki-67 for clinical diagnosis were all from the same paraffin-embedded tissue section. Tissue slices were de-paraffinized with xylene and rehydrated through a grade alcohol series. The endogenous peroxidase activity was blocked by incubation in a 3% hydrogen peroxide solution for 15 minutes. Antigen retrieval was carried out by immersing the slices in 10 mM sodium citrate buffer and maintained at a sub-boiling temperature for 10 minutes. The slices were rinsed in PBS and incubated with 10% normal goat serum to block non-specific staining. The slices were then incubated with 1 μm CUEDC2 antibodies overnight in a humidified chamber. The slices were then processed according to DAB kit and taken photos. All staining processes were assessed by pathologist blinded method. The scoring standard uses the widely accepted semi-quantitative method, taking into account both staining intensity and extent of staining. According to staining intensity (no staining=0, weak staining=1, moderate staining=2, strong staining=3) and the extent of staining (0%=0, 1-24%=1, 25-49%=2, 50-74%=3, 75-100%=4), the final score of each biological sample was determined by multiplying the intensity score with the extent of score of stained cells, ranging from 0 to 10. The CUEDC2 protein expression levels were divided into low (0-4), medium (5-8) and high (9-12).

Figures 6A, 6B:
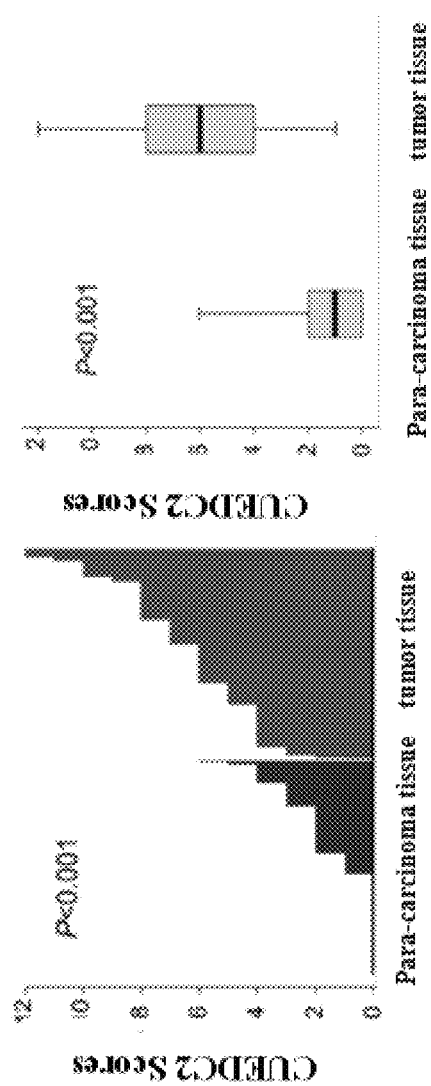
FIG. 6a shows the expression levels of CUEDC2 in para-carcinoma tissue and in tumor tissue.
FIG. 6b is a boxplot graph showing results from FIG. 6a, FIG. 6c shows staining results of 3 representative cases.
Figure 6C:
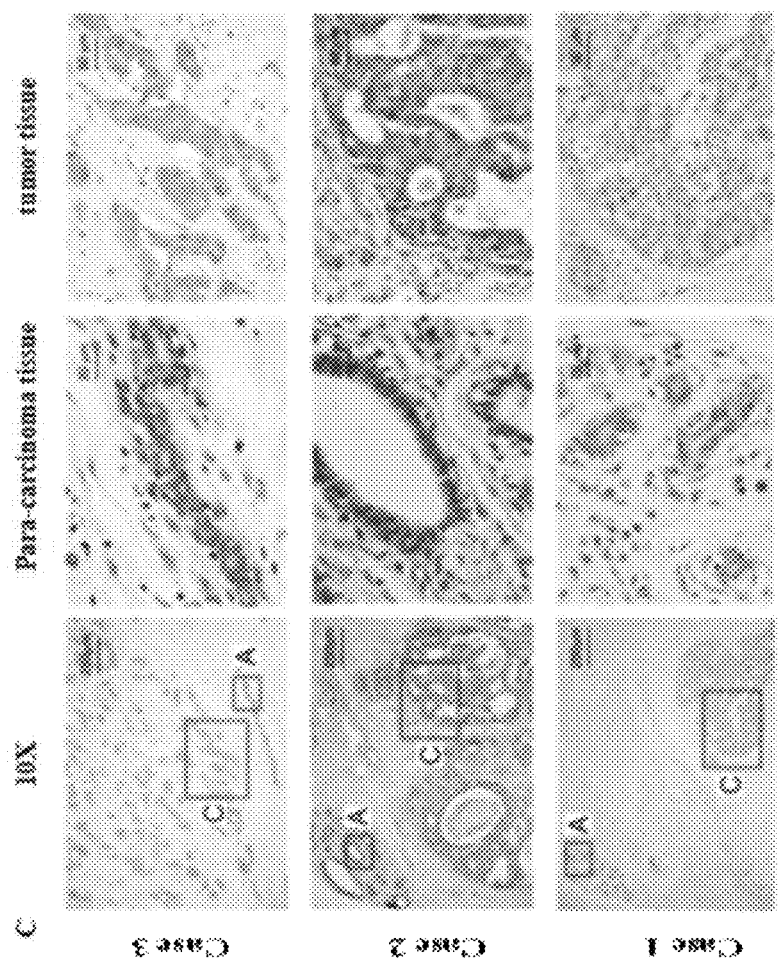
Figure 6D:
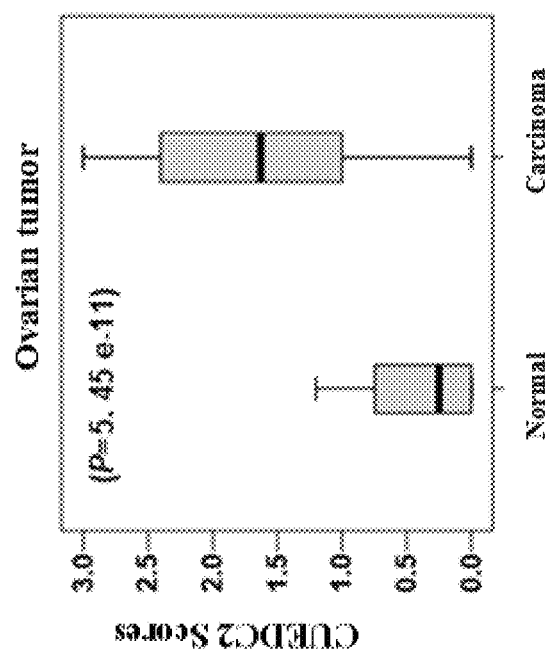
FIG. 6d shows the expression level of CUEDC2 in ovarian tumor tissue.
Figure 7:
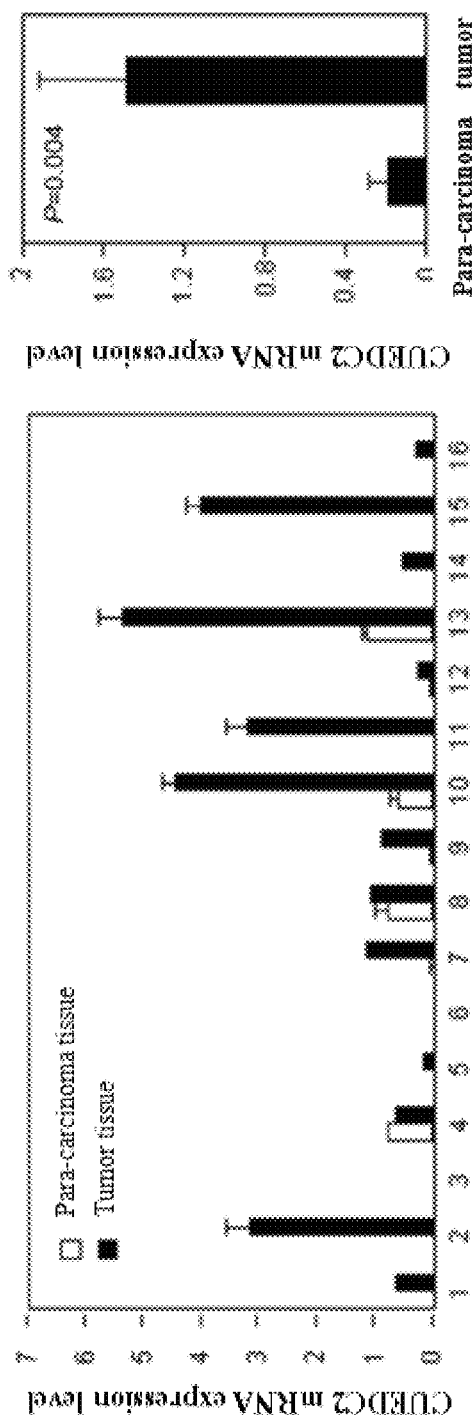
FIG. 7 depicts that the expression level of CUEDC2 mRNA is also significantly elevated in breast cancer tumor tissue.

III. The Result:

The inventors performed immunohistochemical analysis to 449 breast cancer cases, and the results showed that (see table 2) the CUEDC2 expression levels in breast cancer tumor tissues were significantly higher than in normal para-carcinoma tissues (FIG. 6a, b and c, P<0.001). The resulting tissue microarrays showed that, the CUEDC2 expression levels in ovarian tumor tissues were significantly higher than in normal tissues (FIG. 6d). Randomly selected 16 cases from the 449 breast cancer cases to extract RNA, reverse transcribed the RNA and then analyzed the expression levels of CUEDC2 mRNA in tumor tissues and in para-carcinoma tissues by the real-time quantitative PCR analysis method, the results showed that, the expression levels of CUEDC2 mRNA in breast cancer tumor tissues were also significantly increased (FIG. 7, P=0.004). All results above proved that the CUEDC2 expression level in tumor tissues was increased

TABLE 2

Immunohistochemical Analysis Results for the Breast Cancer Cases

| Cancer Name | Serial No. | Gender | Age | CUET | CUEP | Ki-67 | HER-1 | HER-2 | ER | PR |
|---|---|---|---|---|---|---|---|---|---|---|
| Breast cancer | 1 | Female | 52 | 7 | 0 | 0.3 | 0 | 12 | 0 | 0 |
| Breast cancer | 2 | Female | 31 | 8 | 0 | 0.3 | 0 | 12 | 0 | 0 |
| Breast cancer | 3 | Female | 61 | 4 | 0 | 0.15 | 0 | 12 | 0 | 0 |
| Breast cancer | 4 | Female | 44 | 12 | 0 | 0.1 | 2 | 12 | 0 | 0 |
| Breast cancer | 5 | Female | 47 | 8 | 2 | 0.03 | 0 | 2 | 3 | 3 |
| Breast cancer | 6 | Female | 46 | 4 | 2 | 0.15 | 0 | 12 | 0 | 3 |
| Breast cancer | 7 | Female | 64 | 4 | 0 | 0.1 | 0 | 3 | 9 | 0 |
| Breast cancer | 8 | Female | 36 | 3 | 1 | 0.05 | 0 | 0 | 3 | 9 |
| Breast cancer | 9 | Female | 51 | 10 | 4 | 0.05 | 0 | 9 | 0 | 0 |
| Breast cancer | 10 | Female | 42 | 2 | 3 | 0.2 | 0 | 9 | 0 | 0 |
| Breast cancer | 11 | Female | 51 | 4 | 4 | 0.1 | 0 | 0 | 6 | 0 |
| Breast cancer | 12 | Female | 53 | 80 | 3 | 0.6 | 0 | 3 | 0 | 0 |
| Breast cancer | 13 | Female | 42 | 7 | 0 | 0.2 | 0 | 3 | 8 | 6 |
| Breast cancer | 14 | Female | 66 | 8 | 0 | 0.2 | 0 | 0 | 8 | 8 |
| Breast cancer | 15 | Female | 42 | 4 | 1 | 0.03 | 0 | 0 | 6 | 12 |
| Breast cancer | 16 | Female | 34 | 5 | 3 | 0.1 | 0 | 9 | 0 | 2 |
| Breast cancer | 17 | Female | 49 | 7 | 4 | 0.05 | 0 | 0 | 6 | 12 |
| Breast cancer | 18 | Female | 51 | 6 | 3 | 0.15 | 0 | 9 | 0 | 0 |
| Breast cancer | 19 | Female | 44 | 7 | 4 | 0.5 | 0 | 12 | 2 | 2 |
| Breast cancer | 20 | Female | 53 | 8 | 2 | 0.05 | 0 | 4 | 2 | 9 |
| Breast cancer | 21 | Female | 33 | 3 | 0 | 0.03 | 0 | 6 | 0 | 0 |
| Breast cancer | 22 | Female | 36 | 8 | 2 | 0.15 | 0 | 6 | 4 | 2 |
| Breast cancer | 23 | Female | 53 | 3 | 0 | 0.03 | 0 | 6 | 12 | 6 |
| Breast cancer | 24 | Female | 71 | 4 | 1 | 0.05 | 0 | 0 | 6 | 12 |
| Breast cancer | 25 | Female | 42 | 8 | 4 | 0.3 | 2 | 12 | 0 | 0 |
| Breast cancer | 26 | Female | 53 | 7 | 2 | 0.02 | 0 | 0 | 4 | 9 |
| Breast cancer | 27 | Female | 37 | 8 | 0 | 0.3 | 0 | 12 | 0 | 0 |
| Breast cancer | 28 | Female | 55 | 10 | 0 | 0.1 | 0 | 12 | 0 | 2 |
| Breast cancer | 29 | Female | 62 | 8 | 2 | 0.3 | 0 | 12 | 0 | 9 |

TABLE 2-continued

Immunohistochemical Analysis Results for the Breast Cancer Cases

| Cancer Name | Serial No. | Gender | Age | CUET | CUEP | Ki-67 | HER-1 | HER-2 | ER | PR |
|---|---|---|---|---|---|---|---|---|---|---|
| Breast cancer | 30 | Female | 54 | 4 | 0 | 0.2 | 0 | 9 | 0 | 0 |
| Breast cancer | 31 | Female | 40 | 5 | 3 | 0.1 | 0 | 6 | 4 | 9 |
| Breast cancer | 32 | Female | 50 | 6 | 2 | 0.3 | 4 | 4 | 0 | 3 |
| Breast cancer | 33 | Female | 52 | 4 | 0 | 0.15 | 0 | 12 | 0 | 0 |
| Breast cancer | 34 | Female | 44 | 6 | 0 | 0.1 | 0 | 4 | 4 | 9 |
| Breast cancer | 35 | Female | 48 | 6 | 4 | 0.1 | 3 | 12 | 0 | 4 |
| Breast cancer | 36 | Female | 53 | 6 | 2 | 0.05 | 0 | 2 | 0 | 0 |
| Breast cancer | 37 | Female | 36 | 3 | 0 | 0.05 | 0 | 2 | 4 | 9 |
| Breast cancer | 38 | Female | 34 | 4 | 2 | 0.3 | 0 | 3 | 0 | 0 |
| Breast cancer | 39 | Female | 69 | 4 | 3 | 0.03 | 0 | 9 | 0 | 0 |
| Breast cancer | 40 | Female | 44 | 8 | 3 | 0.5 | 0 | 12 | 0 | 0 |
| Breast cancer | 41 | Female | 54 | 8 | 3 | 0.05 | 0 | 9 | 0 | 0 |
| Breast cancer | 42 | Female | 44 | 4 | 2 | 0.03 | 0 | 9 | 0 | 0 |
| Breast cancer | 43 | Female | 40 | 7 | 2 | 0.1 | 0 | 0 | 3 | 3 |
| Breast cancer | 44 | Female | 44 | 8 | 1 | 0.3 | 0 | 12 | 0 | 2 |
| Breast cancer | 45 | Female | 36 | 10 | 2 | 0.4 | 0 | 6 | 0 | 0 |
| Breast cancer | 46 | Female | 39 | 7 | 2 | 0.1 | 0 | 9 | 0 | 0 |
| Breast cancer | 47 | Female | 64 | 9 | 1 | 0.3 | 0 | 12 | 0 | 0 |
| Breast cancer | 48 | Female | 46 | 4 | 2 | 0.4 | 3 | 0 | 0 | 0 |
| Breast cancer | 49 | Female | 48 | 8 | 1 | 0.3 | 3 | 8 | 4 | 2 |
| Breast cancer | 50 | Female | 65 | 5 | 0 | 0.15 | 0 | 12 | 12 | 12 |
| Breast cancer | 51 | Female | 60 | 4 | 0 | 0.05 | 0 | 8 | 12 | 12 |
| Breast cancer | 52 | Female | 46 | 6 | 4 | 0.05 | 0 | 2 | 4 | 12 |
| Breast cancer | 53 | Female | 72 | 6 | 0 | 0.1 | 1 | 2 | 4 | 12 |
| Breast cancer | 54 | Female | 39 | 5 | 0 | 0.02 | 0 | 4 | 9 | 9 |
| Breast cancer | 55 | Female | 50 | 7 | 0 | 0.02 | 0 | 4 | 9 | 9 |
| Breast cancer | 56 | Female | 57 | 4 | 3 | 0.1 | 0 | 0 | 3 | 12 |
| Breast cancer | 57 | Female | 37 | 4 | 0 | 0.1 | 0 | 8 | 12 | 12 |
| Breast cancer | 58 | Female | 52 | 4 | 0 | 0.3 | 0 | 9 | 12 | 9 |
| Breast cancer | 59 | Female | 69 | 8 | 0 | 0.03 | 0 | 8 | 12 | 6 |
| Breast cancer | 60 | Female | 36 | 3 | 0 | 0.15 | 0 | 2 | 4 | 4 |
| Breast cancer | 61 | Female | 62 | 5 | 0 | 0.2 | 0 | 0 | 2 | 0 |
| Breast cancer | 62 | Female | 43 | 4 | 4 | 0.08 | 0 | 0 | 6 | 12 |
| Breast cancer | 63 | Female | 45 | 4 | 0 | 0.1 | 0 | 3 | 3 | 9 |
| Breast cancer | 64 | Female | 72 | 4 | 0 | 0.05 | 0 | 1 | 12 | 12 |
| Breast cancer | 65 | Female | 55 | 4 | 0 | 0.05 | 0 | 2 | 9 | 0 |
| Breast cancer | 66 | Female | 74 | 5 | 2 | 0.1 | 0 | 6 | 12 | 9 |
| Breast cancer | 67 | Female | 52 | 6 | 3 | 0.02 | 0 | 8 | 9 | 6 |
| Breast cancer | 68 | Female | 74 | 5 | 0 | 0.03 | 0 | 12 | 0 | 0 |
| Breast cancer | 69 | Female | 46 | 8 | 0 | 0.05 | 0 | 3 | 9 | 9 |
| Breast cancer | 70 | Female | 48 | 8 | 0 | 0.05 | 0 | 0 | 0 | 9 |
| Breast cancer | 71 | Female | 46 | 4 | 2 | 0.03 | 0 | 0 | 6 | 2 |
| Breast cancer | 72 | Female | 40 | 4 | 4 | 0.02 | 0 | 1 | 9 | 3 |
| Breast cancer | 73 | Female | 39 | 5 | 0 | 0.2 | 0 | 0 | 0 | 8 |
| Breast cancer | 74 | Female | 46 | 3 | 0 | 0.05 | 0 | 1 | 9 | 6 |
| Breast cancer | 75 | Female | 69 | 4 | 3 | 0.05 | 0 | 0 | 6 | 12 |
| Breast cancer | 76 | Female | 40 | 8 | 0 | 0.03 | 0 | 0 | 6 | 9 |
| Breast cancer | 77 | Female | 48 | 5 | 0 | 0.1 | 0 | 8 | 12 | 12 |
| Breast cancer | 78 | Female | 52 | 4 | 0 | 0.1 | 0 | 0 | 8 | 12 |
| Breast cancer | 79 | Female | 53 | 4 | 4 | 0.03 | 0 | 4 | 6 | 0 |
| Breast cancer | 80 | Female | 41 | 4 | 2 | 0.05 | 0 | 0 | 9 | 8 |
| Breast cancer | 81 | Female | 67 | 7 | 0 | 0.05 | 0 | 6 | 6 | 9 |
| Breast cancer | 82 | Female | 54 | 4 | 0 | 0.3 | 0 | 4 | 6 | 9 |
| Breast cancer | 83 | Female | 39 | 4 | 0 | 0.3 | 0 | 9 | 2 | 0 |
| Breast cancer | 84 | Female | 55 | 5 | 0 | 0.3 | 0 | 4 | 9 | 6 |
| Breast cancer | 85 | Female | 37 | 3 | 0 | 0.3 | 0 | 2 | 1 | 12 |
| Breast cancer | 86 | Female | 44 | 6 | 2 | 0.5 | 0 | 9 | 3 | 9 |
| Breast cancer | 87 | Female | 72 | 5 | 1 | 0.2 | 0 | 12 | 9 | 9 |
| Breast cancer | 88 | Female | 55 | 7 | 0 | 0.2 | 0 | 1 | 2 | 3 |
| Breast cancer | 89 | Female | 49 | 4 | 3 | 0.15 | 0 | 12 | 0 | 0 |
| Breast cancer | 90 | Female | 65 | 7 | 0 | 0.15 | 0 | 3 | 12 | 12 |
| Breast cancer | 91 | Female | 52 | 7 | 0 | 0.1 | 0 | 3 | 0 | 9 |
| Breast cancer | 92 | Female | 46 | 7 | 1 | 0.2 | 0 | 8 | 3 | 0 |
| Breast cancer | 93 | Female | 55 | 8 | 0 | 0.02 | 0 | 6 | 9 | 3 |
| Breast cancer | 94 | Female | 64 | 6 | 4 | 0.4 | 2 | 2 | 0 | 0 |
| Breast cancer | 95 | Female | 44 | 6 | 0 | 0.2 | 0 | 12 | 2 | 3 |
| Breast cancer | 96 | Female | 44 | 7 | 0 | 0.5 | 0 | 4 | 4 | 6 |
| Breast cancer | 97 | Female | 45 | 6 | 2 | 0.1 | 0 | 9 | 2 | 9 |
| Breast cancer | 98 | Female | 47 | 8 | 4 | 0.2 | 0 | 12 | 4 | 6 |
| Breast cancer | 99 | Female | 42 | 6 | 2 | 0.3 | 0 | 3 | 2 | 12 |
| Breast cancer | 100 | Female | 36 | 6 | 3 | 0.1 | 0 | 2 | 0 | 6 |
| Breast cancer | 101 | Female | 36 | 6 | 2 | 0.8 | 0 | 0 | 1 | 9 |
| Breast cancer | 102 | Female | 41 | 8 | 0 | 0.3 | 0 | 0 | 0 | 0 |
| Breast cancer | 103 | Female | 44 | 7 | 2 | 0.15 | 0 | 3 | 6 | 12 |
| Breast cancer | 104 | Female | 40 | 12 | 2 | 0.3 | 0 | 12 | 0 | 0 |
| Breast cancer | 105 | Female | 74 | 6 | 2 | 0.2 | 0 | 0 | 12 | 12 |

TABLE 2-continued

Immunohistochemical Analysis Results for the Breast Cancer Cases

| Cancer Name | Serial No. | Gender | Age | CUET | CUEP | Ki-67 | HER-1 | HER-2 | ER | PR |
|---|---|---|---|---|---|---|---|---|---|---|
| Breast cancer | 106 | Female | 45 | 6 | 3 | 0.2 | 0 | 6 | 0 | 9 |
| Breast cancer | 107 | Female | 0 | 4 | 0 | 0.3 | 0 | 9 | 0 | 0 |
| Breast cancer | 108 | Female | 40 | 6 | 3 | 0.3 | 0 | 6 | 4 | 9 |
| Breast cancer | 109 | Female | 56 | 6 | 2 | 0.5 | 0 | 6 | 12 | 6 |
| Breast cancer | 110 | Female | 47 | 12 | 0 | 0.3 | 0 | 3 | 9 | 9 |
| Breast cancer | 111 | Female | 55 | 10 | 0 | 0.5 | 0 | 3 | 6 | 0 |
| Breast cancer | 112 | Female | 49 | 5 | 0 | 0.3 | 0 | 12 | 6 | 0 |
| Breast cancer | 113 | Female | 29 | 10 | 0 | 0.15 | 0 | 12 | 0 | 0 |
| Breast cancer | 114 | Female | 44 | 7 | 2 | 0.3 | 0 | 0 | 6 | 12 |
| Breast cancer | 115 | Female | 41 | 7 | 2 | 0.1 | 0 | 1 | 6 | 9 |
| Breast cancer | 116 | Female | 40 | 8 | 0 | 0.15 | 0 | 0 | 4 | 6 |
| Breast cancer | 117 | Female | 45 | 6 | 4 | 0.4 | 0 | 12 | 0 | 2 |
| Breast cancer | 118 | Female | 36 | 8 | 0 | 0.4 | 0 | 12 | 0 | 0 |
| Breast cancer | 119 | Female | 30 | 3 | 2 | 0.2 | 0 | 0 | 0 | 0 |
| Breast cancer | 120 | Female | 50 | 8 | 0 | 0.1 | 0 | 3 | 12 | 12 |
| Breast cancer | 121 | Female | 46 | 8 | 1 | 0.6 | 0 | 3 | 4 | 0 |
| Breast cancer | 122 | Female | 69 | 8 | 1 | 0.3 | 0 | 12 | 0 | 0 |
| Breast cancer | 123 | Female | 60 | 8 | 0 | 0.1 | 0 | 12 | 6 | 0 |
| Breast cancer | 124 | Female | 35 | 7 | 0 | 0.05 | 0 | 6 | 9 | 9 |
| Breast cancer | 125 | Female | 55 | 4 | 2 | 0.1 | 0 | 9 | 9 | 0 |
| Breast cancer | 126 | Female | 68 | 6 | 0 | 0.3 | 0 | 9 | 12 | 6 |
| Breast cancer | 127 | Female | 37 | 8 | 3 | 0.3 | 0 | 0 | 0 | 12 |
| Breast cancer | 128 | Female | 55 | 6 | 0 | 0.5 | 0 | 12 | 0 | 0 |
| Breast cancer | 129 | Female | 44 | 4 | 0 | 0.5 | 0 | 6 | 9 | 12 |
| Breast cancer | 130 | Female | 39 | 8 | 0 | 0.3 | 0 | 0 | 9 | 9 |
| Breast cancer | 131 | Female | 53 | 8 | 2 | 0.5 | 0 | 0 | 9 | 6 |
| Breast cancer | 132 | Female | 55 | 6 | 0 | 0.15 | 0 | 6 | 12 | 9 |
| Breast cancer | 133 | Female | 61 | 6 | 2 | 0.75 | 3 | 0 | 0 | 0 |
| Breast cancer | 134 | Female | 28 | 8 | 0 | 0.3 | 0 | 12 | 9 | 6 |
| Breast cancer | 135 | Female | 53 | 6 | 0 | 0.03 | 0 | 6 | 12 | 6 |
| Breast cancer | 136 | Female | 46 | 7 | 3 | 0.2 | 0 | 4 | 12 | 9 |
| Breast cancer | 137 | Female | 57 | 8 | 1 | 0.3 | 0 | 12 | 12 | 0 |
| Breast cancer | 138 | Female | 43 | 4 | 3 | 0.5 | 0 | 1 | 9 | 6 |
| Breast cancer | 139 | Female | 68 | 6 | 2 | 0.1 | 0 | 4 | 2 | 0 |
| Breast cancer | 140 | Female | 37 | 6 | 3 | 0.3 | 0 | 4 | 0 | 0 |
| Breast cancer | 141 | Female | 48 | 5 | 1 | 0.15 | 0 | 2 | 6 | 12 |
| Breast cancer | 142 | Female | 46 | 7 | 2 | 0.3 | 0 | 9 | 0 | 0 |
| Breast cancer | 143 | Female | 40 | 8 | 0 | 0.2 | 0 | 0 | 2 | 12 |
| Breast cancer | 144 | Female | 37 | 6 | 4 | 0.3 | 0 | 9 | 2 | 6 |
| Breast cancer | 145 | Female | 72 | 8 | 0 | 0.3 | 0 | 0 | 0 | 0 |
| Breast cancer | 146 | Female | 54 | 12 | 0 | 0.75 | 0 | 12 | 0 | 2 |
| Breast cancer | 147 | Female | 66 | 6 | 0 | 0.3 | 0 | 1 | 6 | 6 |
| Breast cancer | 148 | Female | 54 | 5 | 1 | 0.1 | 0 | 6 | 6 | 6 |
| Breast cancer | 149 | Female | 38 | 6 | 3 | 0.1 | 0 | 6 | 9 | 9 |
| Breast cancer | 150 | Female | 43 | 6 | 0 | 0.15 | 0 | 6 | 9 | 9 |
| Breast cancer | 151 | Female | 39 | 8 | 0 | 0.03 | 0 | 0 | 2 | 6 |
| Breast cancer | 152 | Female | 73 | 5 | 0 | 0.01 | 0 | 9 | 0 | 0 |
| Breast cancer | 153 | Female | 52 | 7 | 0 | 0.05 | 0 | 9 | 0 | 6 |
| Breast cancer | 154 | Female | 79 | 8 | 4 | 0.15 | 0 | 6 | 9 | 12 |
| Breast cancer | 155 | Female | 36 | 1 | 2 | 0.05 | 0 | 2 | 6 | 6 |
| Breast cancer | 156 | Female | 45 | 10 | 0 | 0.4 | 0 | 12 | 0 | 0 |
| Breast cancer | 157 | Female | 62 | 6 | 1 | 0.3 | 0 | 9 | 12 | 12 |
| Breast cancer | 158 | Female | 48 | 4 | 2 | 0.05 | 0 | 0 | 9 | 9 |
| Breast cancer | 159 | Female | 39 | 3 | 0 | 0.3 | 0 | 6 | 0 | 2 |
| Breast cancer | 160 | Female | 54 | 9 | 0 | 0.3 | 0 | 3 | 12 | 12 |
| Breast cancer | 161 | Female | 44 | 6 | 3 | 0.3 | 0 | 0 | 9 | 9 |
| Breast cancer | 162 | Female | 80 | 5 | 0 | 0.3 | 0 | 3 | 12 | 4 |
| Breast cancer | 163 | Female | 59 | 8 | 4 | 0.05 | 0 | 2 | 9 | 9 |
| Breast cancer | 164 | Female | 57 | 8 | 0 | 0.3 | 0 | 0 | 0 | 0 |
| Breast cancer | 165 | Female | 45 | 7 | 0 | 0.2 | 3 | 12 | 0 | 2 |
| Breast cancer | 166 | Female | 43 | 5 | 0 | 0.1 | 0 | 1 | 2 | 6 |
| Breast cancer | 167 | Female | 31 | 4 | 3 | 0.3 | 0 | 8 | 6 | 6 |
| Breast cancer | 168 | Female | 58 | 4 | 0 | 0.4 | 0 | 12 | 0 | 0 |
| Breast cancer | 169 | Female | 33 | 7 | 0 | 0.2 | 0 | 8 | 0 | 6 |
| Breast cancer | 170 | Female | 56 | 10 | 0 | 0.5 | 0 | 12 | 12 | 3 |
| Breast cancer | 171 | Female | 44 | 4 | 0 | 0.7 | 0 | 6 | 0 | 0 |
| Breast cancer | 172 | Female | 55 | 8 | 0 | 0.2 | 0 | 9 | 0 | 0 |
| Breast cancer | 173 | Female | 56 | 10 | 0 | 0.5 | 0 | 12 | 12 | 0 |
| Breast cancer | 174 | Female | 35 | 8 | 1 | 0.3 | 3 | 12 | 4 | 6 |
| Breast cancer | 175 | Female | 60 | 7 | 0 | 0.4 | 0 | 12 | 0 | 6 |
| Breast cancer | 176 | Female | 51 | 12 | 0 | 0.03 | 0 | 12 | 0 | 0 |
| Breast cancer | 177 | Female | 56 | 8 | 0 | 0.6 | 0 | 2 | 0 | 0 |
| Breast cancer | 178 | Female | 50 | 11 | 0 | 0.5 | 0 | 6 | 0 | 0 |
| Breast cancer | 179 | Female | 67 | 12 | 0 | 0.3 | 0 | 12 | 0 | 0 |
| Breast cancer | 180 | Female | 66 | 11 | 3 | 0.5 | 0 | 12 | 0 | 0 |
| Breast cancer | 181 | Female | 55 | 10 | 4 | 0.3 | 0 | 12 | 0 | 0 |

TABLE 2-continued

Immunohistochemical Analysis Results for the Breast Cancer Cases

| Cancer Name | Serial No. | Gender | Age | CUET | CUEP | Ki-67 | HER-1 | HER-2 | ER | PR |
|---|---|---|---|---|---|---|---|---|---|---|
| Breast cancer | 182 | Female | 61 | 6 | 2 | 0.6 | 0 | 6 | 0 | 0 |
| Breast cancer | 183 | Female | 40 | 9 | 3 | 0.6 | 0 | 12 | 2 | 9 |
| Breast cancer | 184 | Female | 53 | 6 | 3 | — | 0 | 0 | 4 | 4 |
| Breast cancer | 185 | Female | 44 | 6 | 0 | 0.4 | 0 | 2 | 9 | 3 |
| Breast cancer | 186 | Female | 45 | 10 | 2 | 0.5 | 2 | 0 | 0 | 0 |
| Breast cancer | 187 | Female | 46 | 12 | 1 | 0.02 | 0 | 2 | 4 | 0 |
| Breast cancer | 188 | Female | 44 | 8 | 0 | 0.4 | 12 | 12 | 0 | 0 |
| Breast cancer | 189 | Female | 68 | 12 | 0 | 0.15 | 4 | 6 | 0 | 0 |
| Breast cancer | 190 | Female | 57 | 4 | 4 | 0.8 | 0 | 8 | 0 | 0 |
| Breast cancer | 191 | Female | 44 | 7 | 3 | 0.6 | 0 | 4 | 0 | 0 |
| Breast cancer | 192 | Female | 82 | 10 | 0 | 0.05 | 0 | 0 | 0 | 0 |
| Breast cancer | 193 | Female | 51 | 7 | 2 | 0.5 | 0 | 12 | 4 | 9 |
| Breast cancer | 194 | Female | 35 | 8 | 3 | 0.7 | 0 | 2 | 0 | 0 |
| Breast cancer | 195 | Female | 35 | 8 | 2 | 0.5 | 0 | 6 | 0 | 9 |
| Breast cancer | 196 | Female | 41 | 10 | 0 | 0.6 | 0 | 12 | 3 | 4 |
| Breast cancer | 197 | Female | 48 | 10 | 0 | 0.5 | 0 | 12 | 0 | 0 |
| Breast cancer | 198 | Female | 63 | 8 | 0 | 0.3 | 0 | 6 | 0 | 0 |
| Breast cancer | 199 | Female | 42 | 8 | 2 | 0.2 | 0 | 0 | 0 | 0 |
| Breast cancer | 200 | Female | 36 | 8 | 0 | 0.3 | 0 | 12 | 0 | 0 |
| Breast cancer | 201 | Female | 35 | 8 | 0 | 0.6 | 0 | 0 | 6 | 6 |
| Breast cancer | 202 | Female | 51 | 4 | 2 | 0.4 | 0 | 9 | 0 | 9 |
| Breast cancer | 203 | Female | 55 | 10 | 1 | 0.3 | 0 | 12 | 0 | 3 |
| Breast cancer | 204 | Female | 55 | 9 | 1 | 0.2 | 0 | 0 | 9 | 0 |
| Breast cancer | 205 | Female | 44 | 12 | 2 | 0.5 | 0 | 12 | 6 | 4 |
| Breast cancer | 206 | Female | 62 | 10 | 3 | 0.6 | 0 | 0 | 0 | 0 |
| Breast cancer | 207 | Female | 66 | 10 | 0.3 | 0 | 12 | 0 | 0 | 0 |
| Breast cancer | 208 | Female | 55 | 6 | 3 | 0.6 | 0 | 0 | 0 | 4 |
| Breast cancer | 209 | Female | 45 | 8 | 2 | 0.4 | 0 | 0 | 0 | 0 |
| Breast cancer | 210 | Female | 46 | 10 | 4 | 0.3 | 0 | 12 | 6 | 12 |
| Breast cancer | 211 | Female | 65 | 11 | 5 | 0.6 | 0 | 12 | 0 | 6 |
| Breast cancer | 212 | Female | 45 | 8 | 2 | 0.5 | 0 | 0 | 0 | 0 |
| Breast cancer | 213 | Female | 70 | 4 | 0 | 0.4 | 0 | 9 | 3 | 0 |
| Breast cancer | 214 | Female | 52 | 10 | 1 | 0.6 | 0 | 1 | 0 | 0 |
| Breast cancer | 215 | Female | 57 | 12 | 0 | 0.3 | 0 | 0 | 0 | 3 |
| Breast cancer | 216 | Female | 61 | 12 | 0 | 0.3 | 0 | 12 | 6 | 0 |
| Breast cancer | 217 | Female | 74 | 10 | 0 | 0.7 | 0 | 6 | 0 | 0 |
| Breast cancer | 218 | Female | 52 | 11 | 3 | 0.7 | 0 | 0 | 0 | 3 |
| Breast cancer | 219 | Female | 41 | 12 | 2 | 0.7 | 0 | 12 | 0 | 3 |
| Breast cancer | 220 | Female | 64 | 10 | 2 | 0.3 | 0 | 6 | 4 | 0 |
| Breast cancer | 221 | Female | 63 | 5 | 3 | 0.1 | 0 | 6 | 0 | 4 |
| Breast cancer | 222 | Female | 45 | 8 | 0 | 0.4 | 0 | 8 | 2 | 2 |
| Breast cancer | 223 | Female | 48 | 10 | 0 | 0.6 | 0 | 10 | 2 | 3 |
| Breast cancer | 224 | Female | 28 | 12 | 0 | 0.5 | 0 | 2 | 0 | 0 |
| Breast cancer | 225 | Female | 52 | 10 | 4 | 0.6 | 2 | 8 | 0 | 2 |
| Breast cancer | 226 | Female | 65 | 4 | 2 | — | 0 | 0 | 0 | 0 |
| Breast cancer | 227 | Female | 43 | 5 | 1 | — | 0 | 0 | 0 | 0 |
| Breast cancer | 228 | Female | 60 | 3 | 2 | 0.05 | 0 | 0 | 0 | 0 |
| Breast cancer | 229 | Female | 42 | 5 | 0 | 0.15 | 0 | 4 | 6 | 3 |
| Breast cancer | 230 | Female | 38 | 5 | 0 | 0.2 | 0 | 4 | 4 | 0 |
| Breast cancer | 231 | Female | 58 | 8 | 0 | 0.7 | 0 | 8 | 3 | 0 |
| Breast cancer | 232 | Female | 37 | 8 | 0 | 0.6 | 0 | 8 | 0 | 0 |
| Breast cancer | 233 | Female | 41 | 8 | 0 | 0.5 | 0 | 8 | 2 | 2 |
| Breast cancer | 234 | Female | 42 | 8 | 0 | 0.7 | 0 | 0 | 0 | 0 |
| Breast cancer | 235 | Female | 52 | 6 | 2 | 0.4 | 0 | 4 | 0 | 0 |
| Breast cancer | 236 | Female | 54 | 6 | 5 | 0.3 | 0 | 6 | 4 | 3 |
| Breast cancer | 237 | Female | 34 | 5 | 3 | 0.2 | 3 | 0 | 0 | 0 |
| Breast cancer | 238 | Female | 71 | 6 | 0 | 0.3 | 0 | 4 | 4 | 0 |
| Breast cancer | 239 | Female | 45 | 6 | 1 | — | 0 | 5 | 0 | 0 |
| Breast cancer | 240 | Female | 41 | 8 | 0 | — | 0 | 0 | 5 | 4 |
| Breast cancer | 241 | Female | 54 | 9 | 0 | — | — | 0 | 1 | 2 |
| Breast cancer | 242 | Female | 43 | 5 | 1 | 0.2 | 0 | 0 | 0 | 0 |
| Breast cancer | 243 | Female | 32 | 5 | 0 | — | 0 | 0 | 3 | 0 |
| Breast cancer | 244 | Female | 59 | 6 | 2 | — | 0 | 0 | 0 | 0 |
| Breast cancer | 245 | Female | 37 | 3 | 2 | — | 0 | 0 | 0 | 0 |
| Breast cancer | 246 | Female | 45 | 10 | 1 | — | 0 | 0 | 6 | 4 |
| Breast cancer | 247 | Female | 59 | 9 | 2 | — | 0 | 0 | 0 | 0 |
| Breast cancer | 248 | Female | 45 | 11 | 2 | 0.25 | 0 | 0 | 0 | 0 |
| Breast cancer | 249 | Female | 46 | 9 | 4 | 0.7 | 0 | 0 | 6 | 0 |
| Breast cancer | 250 | Female | 51 | 4 | 0 | 0.15 | 0 | 6 | 0 | 2 |
| Breast cancer | 251 | Female | 37 | 8 | 3 | 0.2 | 0 | 2 | 4 | 0 |
| Breast cancer | 252 | Female | 45 | 6 | 1 | 0.2 | 3 | 2 | 9 | 6 |
| Breast cancer | 253 | Female | 51 | 10 | 1 | 0.8 | 0 | 0 | 0 | 0 |
| Breast cancer | 254 | Female | 39 | 6 | 0 | 0.4 | 2 | 0 | 9 | 1 |
| Breast cancer | 255 | Female | 46 | 8 | 3 | 0.9 | 0 | 0 | 0 | 0 |
| Breast cancer | 256 | Female | 38 | 7 | 2 | 0.2 | 0 | 4 | 0 | 0 |
| Breast cancer | 257 | Female | 50 | 7 | 0 | 0.5 | 0 | 8 | 0 | 0 |

TABLE 2-continued

Immunohistochemical Analysis Results for the Breast Cancer Cases

| Cancer Name | Serial No. | Gender | Age | CUET | CUEP | Ki-67 | HER-1 | HER-2 | ER | PR |
|---|---|---|---|---|---|---|---|---|---|---|
| Breast cancer | 258 | Female | 64 | 6 | 0 | 0.02 | 0 | 0 | 2 | 0 |
| Breast cancer | 259 | Female | 58 | 6 | 0 | 0.15 | 0 | 0 | 8 | 2 |
| Breast cancer | 260 | Female | 56 | 7 | 6 | 0.6 | 0 | 0 | 2 | 0 |
| Breast cancer | 261 | Female | 46 | 5 | 2 | 0.3 | 0 | 6 | 2 | 2 |
| Breast cancer | 262 | Female | 53 | 7 | 0 | 0.7 | 3 | 12 | 0 | 0 |
| Breast cancer | 263 | Female | 40 | 4 | 2 | — | 0 | 12 | 2 | 2 |
| Breast cancer | 264 | Female | 69 | 8 | 0 | 0.3 | 0 | 8 | 0 | 0 |
| Breast cancer | 265 | Female | 47 | 8 | 4 | 0.3 | 0 | 8 | 8 | 6 |
| Breast cancer | 266 | Female | 50 | 11 | 1 | 0.4 | 0 | 12 | 0 | 0 |
| Breast cancer | 267 | Female | 49 | 7 | 0 | 0.4 | 0 | 6 | 2 | 12 |
| Breast cancer | 268 | Female | 55 | 4 | 2 | 0.7 | 0 | 8 | 0 | 0 |
| Breast cancer | 269 | Female | 49 | 6 | 2 | 0.2 | 0 | 4 | 1 | 2 |
| Breast cancer | 270 | Female | 60 | 4 | 6 | 0.03 | 4 | 0 | 4 | 0 |
| Breast cancer | 271 | Female | 56 | 4 | 0 | 0.3 | 0 | 0 | 6 | 2 |
| Breast cancer | 272 | Female | 49 | 4 | 2 | 0.02 | 0 | 0 | 8 | 8 |
| Breast cancer | 273 | Female | 26 | 8 | 0 | 0.4 | 0 | 0 | 0 | 0 |
| Breast cancer | 274 | Female | 50 | 4 | 0 | 0.2 | 0 | 0 | 6 | 0 |
| Breast cancer | 275 | Female | 55 | 10 | 0 | 0.5 | 0 | 12 | 0 | 0 |
| Breast cancer | 276 | Female | 40 | 8 | 0 | 0.7 | 0 | 8 | 2 | 9 |
| Breast cancer | 277 | Female | 69 | 4 | 0.05 | 0 | 0 | 0 | 0 | |
| Breast cancer | 278 | Female | 33 | 2 | 0 | 0.02 | 0 | 0 | 12 | 6 |
| Breast cancer | 279 | Female | 59 | 7 | 0 | 0.15 | 0 | 0 | 3 | 0 |
| Breast cancer | 280 | Female | 64 | 4 | 0 | 0.25 | 0 | 0 | 0 | 0 |
| Breast cancer | 281 | Female | 84 | 5 | 1 | 0.6 | 0 | 0 | 0 | 0 |
| Breast cancer | 282 | Female | 35 | 8 | 2 | 0.6 | 0 | 4 | 5 | 4 |
| Breast cancer | 283 | Female | 38 | 6 | 0 | 0.05 | 0 | 0 | 8 | 12 |
| Breast cancer | 284 | Female | 48 | 8 | 2 | 0.6 | 0 | 2 | 0 | 0 |
| Breast cancer | 285 | Female | 51 | 9 | 3 | — | 3 | 8 | 0 | 0 |
| Breast cancer | 286 | Female | 27 | 10 | 4 | — | 0 | 12 | 0 | 1 |
| Breast cancer | 287 | Female | 48 | 6 | 2 | 0.15 | 8 | 12 | 0 | 0 |
| Breast cancer | 288 | Female | 47 | 8 | 2 | 0.3 | 0 | 7 | 4 | 2 |
| Breast cancer | 289 | Female | 50 | 5 | 2 | 0.05 | 0 | 2 | 6 | 4 |
| Breast cancer | 290 | Female | 43 | 7 | 0 | 0.15 | 2 | 0 | 6 | 6 |
| Breast cancer | 291 | Female | 41 | 4 | 2 | 0.03 | 0 | 0 | 12 | 8 |
| Breast cancer | 292 | Female | 46 | 6 | 3 | 0.2 | 0 | 0 | 7 | 6 |
| Breast cancer | 293 | Female | 64 | 4 | 0 | 0.1 | 0 | 0 | 8 | 4 |
| Breast cancer | 294 | Female | 44 | 4 | 2 | 0.15 | 0 | 0 | 9 | 12 |
| Breast cancer | 295 | Female | 48 | 6 | 0 | 0.2 | 0 | 0 | 0 | 0 |
| Breast cancer | 296 | Female | 30 | 6 | 1 | 0.05 | 2 | 4 | 2 | 3 |
| Breast cancer | 297 | Female | 57 | 6 | 2 | 0.3 | 0 | 0 | 5 | 0 |
| Breast cancer | 298 | Female | 63 | 7 | 2 | 0.15 | 0 | 4 | 6 | 4 |
| Breast cancer | 299 | Female | 64 | 6 | 0 | 0.2 | 0 | 0 | 6 | 0 |
| Breast cancer | 300 | Female | 38 | 8 | 3 | 0.1 | 0 | 0 | 0 | 0 |
| Breast cancer | 301 | Female | 32 | 4 | 0 | 0.05 | 0 | 0 | 12 | 6 |
| Breast cancer | 302 | Female | 66 | 4 | 4 | 0.1 | 0 | 0 | 6 | 6 |
| Breast cancer | 303 | Female | 53 | 4 | 2 | 0.2 | 0 | 4 | 6 | 4 |
| Breast cancer | 304 | Female | 43 | 6 | 0 | 0.15 | 0 | 6 | 0 | 0 |
| Breast cancer | 305 | Female | 47 | 4 | 0 | 0.05 | 0 | 0 | 2 | 2 |
| Breast cancer | 306 | Female | 53 | 8 | 2 | 0.4 | 3 | 8 | 0 | 0 |
| Breast cancer | 307 | Female | 52 | 6 | 3 | 0.5 | 0 | 8 | 0 | 6 |
| Breast cancer | 308 | Female | 47 | 6 | 1 | 0.2 | 0 | 0 | 2 | 2 |
| Breast cancer | 309 | Female | 66 | 10 | 0 | 0.2 | 0 | 0 | 0 | 6 |
| Breast cancer | 310 | Female | 44 | 4 | 0 | 0.15 | 0 | 0 | 0 | 4 |
| Breast cancer | 311 | Female | 80 | 6 | 2 | 0.2 | 0 | 0 | 6 | 0 |
| Breast cancer | 312 | Female | 60 | 8 | 0 | 0.4 | 0 | 0 | 8 | 2 |
| Breast cancer | 313 | Female | 50 | 6 | 1 | 0.3 | 0 | 0 | 6 | 6 |
| Breast cancer | 314 | Female | 55 | 5 | 2 | 0.1 | 0 | 0 | 6 | 4 |
| Breast cancer | 315 | Female | 42 | 5 | 0 | 0.15 | 2 | 0 | 0 | 0 |
| Breast cancer | 316 | Female | 28 | 6 | 0 | 0.2 | 0 | 6 | 0 | 2 |
| Breast cancer | 317 | Female | 49 | 3 | 3 | 0.1 | 0 | 4 | 4 | 4 |
| Breast cancer | 318 | Female | 60 | 4 | 2 | 0.15 | 0 | 0 | 6 | 4 |
| Breast cancer | 319 | Female | 48 | 5 | 4 | 0.3 | 0 | 4 | 0 | 0 |
| Breast cancer | 320 | Female | 47 | 7 | 0 | 0.2 | 0 | 0 | 3 | 6 |
| Breast cancer | 321 | Female | 51 | 4 | 0 | 0.15 | 0 | 0 | 6 | 9 |
| Breast cancer | 322 | Female | 56 | 6 | 2 | 0.3 | 0 | 0 | 0 | 0 |
| Breast cancer | 323 | Female | 39 | 5 | 2 | 0.2 | 0 | 0 | 0 | 0 |
| Breast cancer | 324 | Female | 65 | 8 | 0 | 0.4 | 0 | 6 | 4 | 0 |
| Breast cancer | 325 | Female | 45 | 4 | 2 | 0.1 | 0 | 0 | 2 | 0 |
| Breast cancer | 326 | Female | 52 | 8 | 2 | 0.5 | 0 | 0 | 0 | 0 |
| Breast cancer | 327 | Female | 57 | 12 | 1 | 0.6 | 0 | 6 | 0 | 0 |
| Breast cancer | 328 | Female | 42 | 7 | 0 | 0.3 | 0 | 6 | 0 | 0 |
| Breast cancer | 329 | Female | 44 | 5 | 3 | 0.3 | 0 | 6 | 0 | 0 |
| Breast cancer | 330 | Female | 55 | 8 | 2 | 0.1 | 0 | 0 | 2 | 0 |
| Breast cancer | 331 | Female | 60 | 7 | 0 | 0.4 | 0 | 3 | 12 | 4 |
| Breast cancer | 332 | Female | 52 | 4 | 4 | 0.3 | 0 | 6 | 0 | 0 |
| Breast cancer | 333 | Female | 55 | 8 | 5 | 0.3 | 0 | 9 | 0 | 0 |

TABLE 2-continued

Immunohistochemical Analysis Results for the Breast Cancer Cases

| Cancer Name | Serial No. | Gender | Age | CUET | CUEP | Ki-67 | HER-1 | HER-2 | ER | PR |
|---|---|---|---|---|---|---|---|---|---|---|
| Breast cancer | 334 | Female | 43 | 10 | 0 | 0.7 | 3 | 8 | 4 | 2 |
| Breast cancer | 335 | Female | 58 | 4 | 1 | — | — | 0 | 9 | 12 |
| Breast cancer | 336 | Female | 44 | 11 | 1 | 0.05 | 0 | 4 | 0 | 0 |
| Breast cancer | 337 | Female | 0 | 7 | 0 | 0.2 | 0 | 3 | 0 | 0 |
| Breast cancer | 338 | Female | 61 | 4 | 4 | 0.15 | 0 | 0 | 6 | 4 |
| Breast cancer | 339 | Female | 52 | 4 | 3 | 0.1 | 0 | 0 | 9 | 9 |
| Breast cancer | 340 | Female | 43 | 6 | 1 | 0.2 | 0 | 3 | 9 | 6 |
| Breast cancer | 341 | Female | 49 | 5 | 4 | 0.1 | 0 | 0 | 4 | 0 |
| Breast cancer | 342 | Female | 50 | 4 | 2 | 0.15 | 0 | 0 | 8 | 2 |
| Breast cancer | 343 | Female | 67 | 3 | 0 | 0.4 | 0 | 4 | 12 | 12 |
| Breast cancer | 344 | Female | 60 | 7 | 3 | 0.3 | 0 | 9 | 0 | 0 |
| Breast cancer | 345 | Female | 62 | 9 | 4 | 0.4 | 0 | 0 | 0 | 0 |
| Breast cancer | 346 | Female | 46 | 5 | 1 | 0.2 | 0 | 0 | 0 | 0 |
| Breast cancer | 347 | Female | 58 | 8 | 2 | 0.3 | 0 | 9 | 12 | 2 |
| Breast cancer | 348 | Female | 60 | 4 | 0 | 0.2 | 0 | 0 | 4 | 0 |
| Breast cancer | 349 | Female | 48 | 4 | 4 | 0.05 | 0 | 0 | 4 | 0 |
| Breast cancer | 350 | Female | 48 | 12 | 2 | 0.6 | 3 | 6 | 0 | 0 |
| Breast cancer | 351 | Female | 51 | 4 | 4 | 0.05 | 0 | 0 | 6 | 2 |
| Breast cancer | 352 | Female | 36 | 6 | 0 | 0.15 | 0 | 0 | 4 | 0 |
| Breast cancer | 353 | Female | 45 | 6 | 2 | 0.1 | 0 | 0 | 0 | 6 |
| Breast cancer | 354 | Female | 44 | 4 | 0 | 0.2 | 0 | 4 | 4 | 4 |
| Breast cancer | 355 | Female | 51 | 3 | 0 | 0.2 | 0 | 0 | 0 | 0 |
| Breast cancer | 356 | Female | 51 | 5 | 4 | 0.1 | 0 | 0 | 4 | 0 |
| Breast cancer | 357 | Female | 80 | 5 | 0 | 0.2 | 0 | 0 | 0 | 0 |
| Breast cancer | 358 | Female | 69 | 10 | 0 | 0.3 | 0 | 0 | 9 | 6 |
| Breast cancer | 359 | Female | 40 | 7 | 0 | 0.3 | 0 | 4 | 4 | 4 |
| Breast cancer | 360 | Female | 46 | 6 | 2 | 0.2 | 0 | 0 | 2 | 2 |
| Breast cancer | 361 | Female | 43 | 8 | 3 | 0.7 | 0 | 12 | 0 | 0 |
| Breast cancer | 362 | Female | 50 | 4 | 0 | 0.1 | 0 | 0 | 0 | 0 |
| Breast cancer | 363 | Female | 44 | 7 | 0 | 0.3 | 2 | 2 | 6 | 6 |
| Breast cancer | 364 | Female | 51 | 8 | 0 | 0.1 | 0 | 0 | 0 | 0 |
| Breast cancer | 365 | Female | 52 | 3 | 2 | 0.2 | 0 | 0 | 8 | 4 |
| Breast cancer | 366 | Female | 70 | 5 | 0 | 0.02 | 0 | 0 | 8 | 8 |
| Breast cancer | 367 | Female | 45 | 6 | 1 | 0.01 | 3 | 0 | 4 | 12 |
| Breast cancer | 368 | Female | 51 | 7 | 0 | 0.7 | 0 | 7 | 0 | 4 |
| Breast cancer | 369 | Female | 33 | 8 | 0 | 0.03 | 0 | 6 | 0 | 0 |
| Breast cancer | 370 | Female | 53 | 2 | 0 | 0.4 | 0 | 8 | 6 | 0 |
| Breast cancer | 371 | Female | 74 | 3 | 1 | 0.2 | 0 | 4 | 6 | 0 |
| Breast cancer | 372 | Female | 50 | 3 | 0 | 0.1 | 0 | 0 | 12 | 3 |
| Breast cancer | 373 | Female | 51 | 6 | 0 | 0.2 | 0 | 0 | 2 | 6 |
| Breast cancer | 374 | Female | 62 | 5 | 1 | 0.1 | 0 | 4 | 0 | 0 |
| Breast cancer | 375 | Female | 75 | 6 | 0 | 0.3 | 0 | 3 | 12 | 6 |
| Breast cancer | 376 | Female | 0 | 6 | 2 | 0.3 | 0 | 4 | 0 | 0 |
| Breast cancer | 377 | Female | 52 | 10 | 2 | 0.3 | 0 | 4 | 0 | 0 |
| Breast cancer | 378 | Female | 47 | 8 | 5 | 0.3 | 4 | 8 | 4 | 2 |
| Breast cancer | 379 | Female | 64 | 5 | 1 | 0.02 | 0 | 0 | 12 | 8 |
| Breast cancer | 380 | Female | 45 | 12 | 4 | 0.3 | 0 | 12 | 0 | 0 |
| Breast cancer | 381 | Female | 39 | 4 | 0 | 0.05 | 0 | 12 | 0 | 0 |
| Breast cancer | 382 | Female | 51 | 7 | 2 | 0.2 | 0 | 12 | 0 | 0 |
| Breast cancer | 383 | Female | 47 | 8 | 0 | 0.5 | 0 | 8 | 0 | 0 |
| Breast cancer | 384 | Female | 48 | 10 | 2 | 0.7 | 0 | 4 | 2 | 6 |
| Breast cancer | 385 | Female | 48 | 10 | 0 | 0.4 | 0 | 0 | 0 | 8 |
| Breast cancer | 386 | Female | 39 | 4 | 4 | 0.2 | 0 | 0 | 0 | 0 |
| Breast cancer | 387 | Female | 49 | 4 | 4 | — | 0 | 0 | 0 | 0 |
| Breast cancer | 388 | Female | 31 | 7 | 2 | 0.05 | 0 | 0 | 0 | 0 |
| Breast cancer | 389 | Female | 73 | 4 | 0 | 0.02 | 0 | 0 | 12 | 0 |
| Breast cancer | 390 | Female | 55 | 6 | 0 | 0.1 | 0 | 12 | 0 | 0 |
| Breast cancer | 391 | Female | 42 | 12 | 0 | 0.5 | 0 | 12 | 0 | 6 |
| Breast cancer | 392 | Female | 37 | 7 | 2 | 0.1 | 0 | 0 | 4 | 6 |
| Breast cancer | 393 | Female | 64 | 2 | 0 | 0.15 | 1 | 1 | 12 | 0 |
| Breast cancer | 394 | Female | 48 | 6 | 2 | — | 2 | 6 | 0 | 1 |
| Breast cancer | 395 | Female | 50 | 7 | 3 | — | 0 | 12 | 0 | 0 |
| Breast cancer | 396 | Female | 50 | 4 | 0 | — | 0 | 1 | 4 | 6 |
| Breast cancer | 397 | Female | 49 | 6 | 2 | — | 0 | 0 | 8 | 8 |
| Breast cancer | 398 | Female | 46 | 6 | 0 | 0.3 | 0 | 0 | 8 | 0 |
| Breast cancer | 399 | Female | 53 | 4 | 0 | 0.05 | 0 | 1 | 12 | 6 |
| Breast cancer | 400 | Female | 0 | 7 | 1 | 0.05 | 0 | 0 | 12 | 9 |
| Breast cancer | 401 | Female | 52 | 4 | 0 | 0.2 | 0 | 12 | 0 | 0 |
| Breast cancer | 402 | Female | 62 | 4 | 4 | 0 | 0 | 2 | 0 | 0 |
| Breast cancer | 403 | Female | 46 | 10 | 2 | 0.3 | 0 | 8 | 0 | 0 |
| Breast cancer | 404 | Female | 51 | 2 | 1 | 0.02 | 0 | 0 | 2 | 6 |
| Breast cancer | 405 | Female | 57 | 5 | 0 | — | 0 | 12 | 0 | 0 |
| Breast cancer | 406 | Female | 58 | 9 | 0 | 0.4 | 0 | 12 | 0 | 0 |
| Breast cancer | 407 | Female | 61 | 8 | 0 | — | 0 | 0 | 8 | 0 |
| Breast cancer | 408 | Female | 33 | 10 | 3 | 0.05 | 0 | 6 | 0 | 0 |
| Breast cancer | 409 | Female | 47 | 4 | 2 | 0.2 | 0 | 0 | 3 | 0 |

TABLE 2-continued

Immunohistochemical Analysis Results for the Breast Cancer Cases

| Cancer Name | Serial No. | Gender | Age | CUET | CUEP | Ki-67 | HER-1 | HER-2 | ER | PR |
|---|---|---|---|---|---|---|---|---|---|---|
| Breast cancer | 410 | Female | 47 | 6 | 6 | 0 | 0 | 0 | 0 | 4 |
| Breast cancer | 411 | Female | 58 | 7 | 3 | 0.6 | 0 | 8 | 0 | 6 |
| Breast cancer | 412 | Female | 63 | 6 | 0 | 0.1 | 0 | 0 | 2 | 0 |
| Breast cancer | 413 | Female | 46 | 6 | 2 | 0.02 | 4 | 4 | 4 | 2 |
| Breast cancer | 414 | Female | 69 | 6 | 0 | 0.1 | 0 | 0 | 8 | 8 |
| Breast cancer | 415 | Female | 54 | 5 | 2 | 0.6 | 0 | 12 | 0 | 0 |
| Breast cancer | 416 | Female | 39 | 3 | 3 | 0.2 | 0 | 4 | 6 | 4 |
| Breast cancer | 417 | Female | 55 | 7 | 0 | 0.1 | 0 | 12 | 2 | 0 |
| Breast cancer | 418 | Female | 69 | 8 | 0 | 0.2 | 0 | 0 | 0 | 0 |
| Breast cancer | 419 | Female | 37 | 6 | 3 | 0.3 | 0 | 0 | 10 | 12 |
| Breast cancer | 420 | Female | 56 | 7 | 0 | 0.4 | 0 | 0 | 2 | 2 |
| Breast cancer | 421 | Female | 75 | 4 | 2 | 0.01 | 0 | 0 | 12 | 8 |
| Breast cancer | 422 | Female | 58 | 6 | 0 | 0.1 | 0 | 0 | 4 | 0 |
| Breast cancer | 423 | Female | 51 | 2 | 3 | 0.02 | 0 | 1 | 12 | 0 |
| Breast cancer | 424 | Female | 68 | 1 | 1 | 0.2 | 0 | 0 | 8 | 4 |
| Breast cancer | 425 | Female | 35 | 5 | 1 | 0.02 | 0 | 0 | 1 | 3 |
| Breast cancer | 426 | Female | 61 | 5 | 0 | 0.02 | 0 | 0 | 2 | 2 |
| Breast cancer | 427 | Female | 60 | 7 | 0 | 0.02 | 0 | 0 | 0 | 0 |
| Breast cancer | 428 | Female | 56 | 5 | 0 | 0.05 | 0 | 0 | 8 | |
| Breast cancer | 429 | Female | 35 | 4 | 0 | 0.01 | 1 | 0 | 0 | 4 |
| Breast cancer | 430 | Female | 66 | 11 | 0 | 0.1 | 0 | 6 | 0 | 0 |
| Breast cancer | 431 | Female | 52 | 6 | 0 | 0.3 | 12 | 1 | 0 | 0 |
| Breast cancer | 432 | Female | 77 | 4 | 0 | 0.02 | 0 | 0 | 12 | 6 |
| Breast cancer | 433 | Female | 50 | 4 | 3 | 0.01 | 0 | 0 | 0 | 6 |
| Breast cancer | 434 | Female | 40 | 4 | 4 | 0.05 | 3 | 0 | 0 | 0 |
| Breast cancer | 435 | Female | 67 | 7 | 3 | 0.01 | 0 | 0 | 2 | 0 |
| Breast cancer | 436 | Female | 56 | 4 | 2 | 0.05 | 0 | 0 | 0 | 0 |
| Breast cancer | 437 | Female | 49 | 6 | 0 | 0.05 | 0 | 0 | 0 | 0 |
| Breast cancer | 438 | Female | 55 | 8 | 0 | 0.05 | 0 | 12 | 4 | 2 |
| Breast cancer | 439 | Female | 51 | 8 | 2 | 0.3 | 0 | 0 | 0 | 0 |
| Breast cancer | 440 | Female | 30 | 8 | 0 | 0.05 | 0 | 0 | 6 | 0 |
| Breast cancer | 441 | Female | 46 | 4 | 0 | 0.1 | 0 | 0 | 6 | 12 |
| Breast cancer | 442 | Female | 43 | 4 | 0 | 0.6 | 0 | 0 | 4 | 9 |
| Breast cancer | 443 | Female | 41 | 5 | 0 | 0.05 | 0 | 0 | 12 | 12 |
| Breast cancer | 444 | Female | 44 | 5 | 2 | 0.3 | 0 | 0 | 0 | 0 |
| Breast cancer | 445 | Female | 49 | 4 | 1 | 0.01 | 0 | 0 | 8 | 6 |
| Breast cancer | 446 | Female | 47 | 4 | 2 | 0.01 | 0 | 0 | 8 | 12 |
| Breast cancer | 447 | Female | 48 | 6 | 0 | — | 0 | 4 | 3 | 1 |
| Breast cancer | 448 | Female | 57 | 10 | 4 | 0.4 | 0 | 0 | 8 | 4 |
| Breast cancer | 449 | Female | 60 | 7 | 4 | 0.02 | 0 | 9 | 0 | 0 |

According to above experiment method, the inventors further detected that the expression level of CUEDC2 in ovarian tumor is high expression level too.

Embodiment 3: Inverse Correlation of CUEDC2 with ERα in Breast Cancer

I. The material: the same as that in the embodiment 2.

Figure 8:
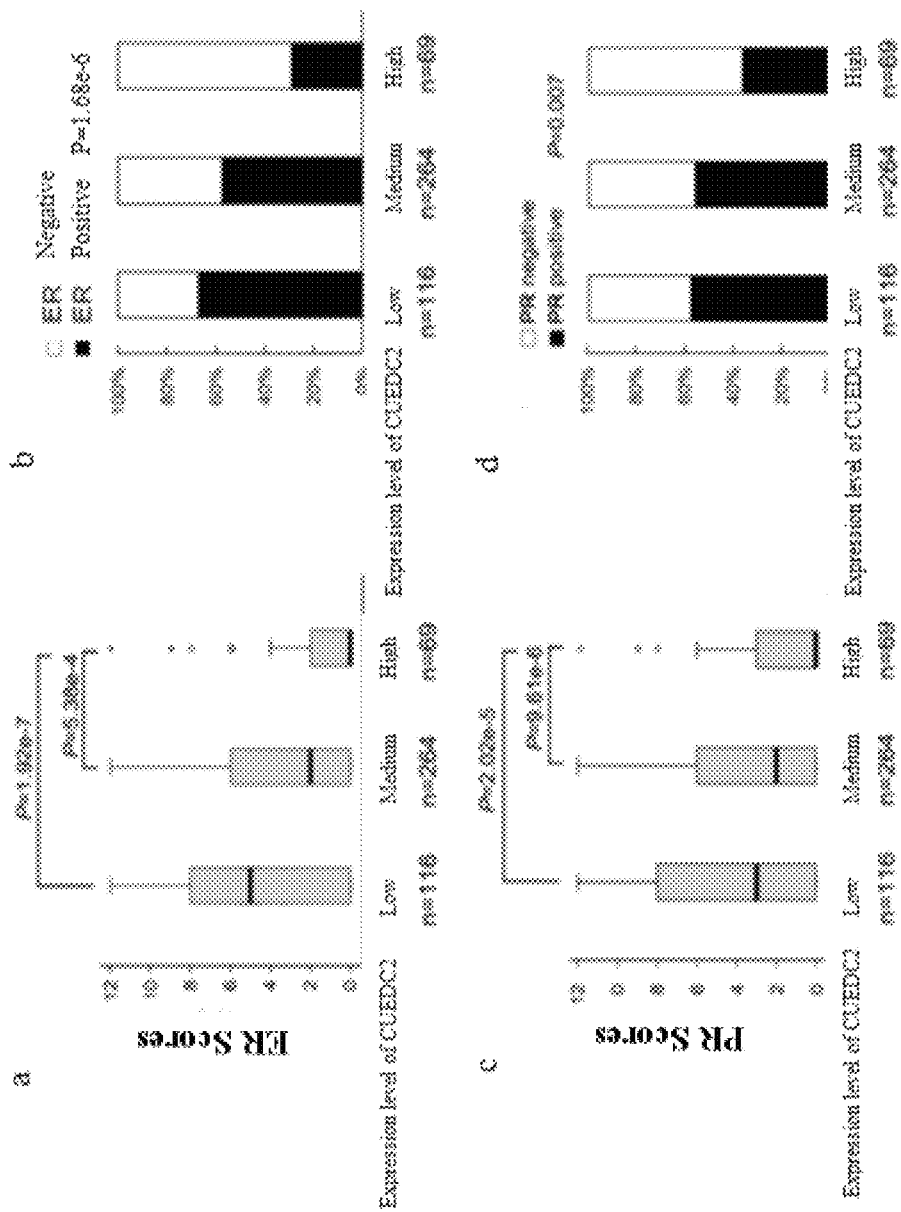
Figure 10B:
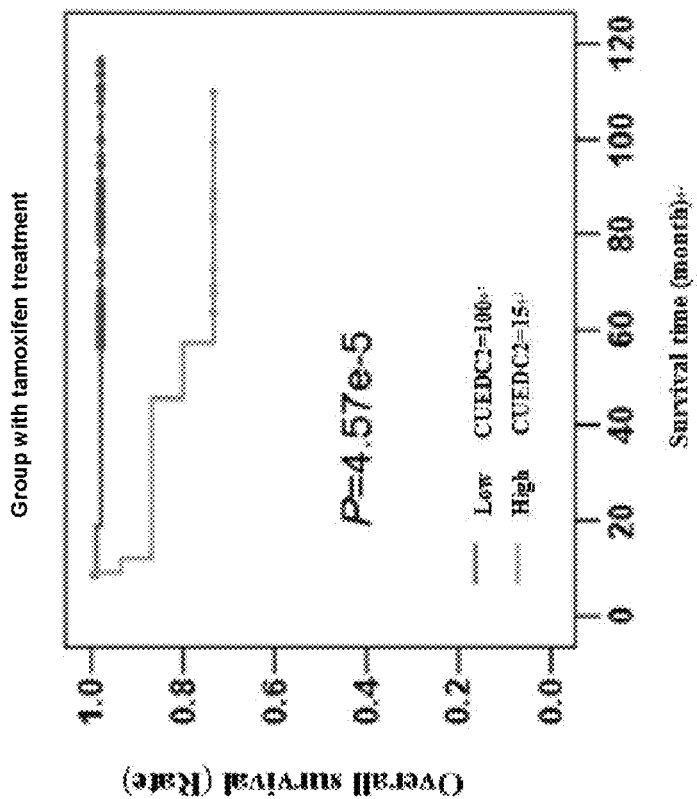
FIG. 10b shows overall survival curves of patients who received tamoxifen, describing that, among these patients, patients with higher CUEDC2 expression have higher disease-free survival rates and overall survival rates than patients with lower CUEDC2 expression.
Figure 10A:
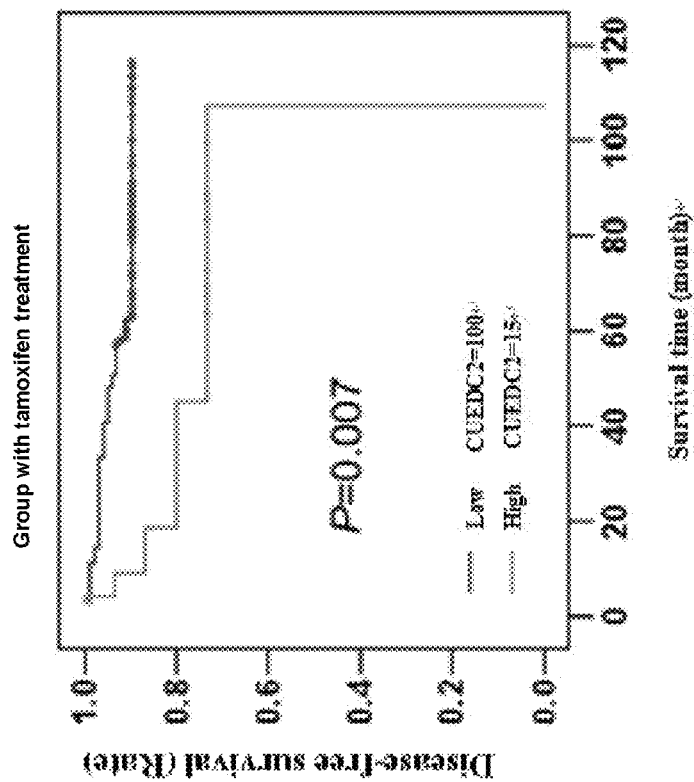
FIG. 10a shows survival curves of patients who received tamoxifen.
Figure 11B:
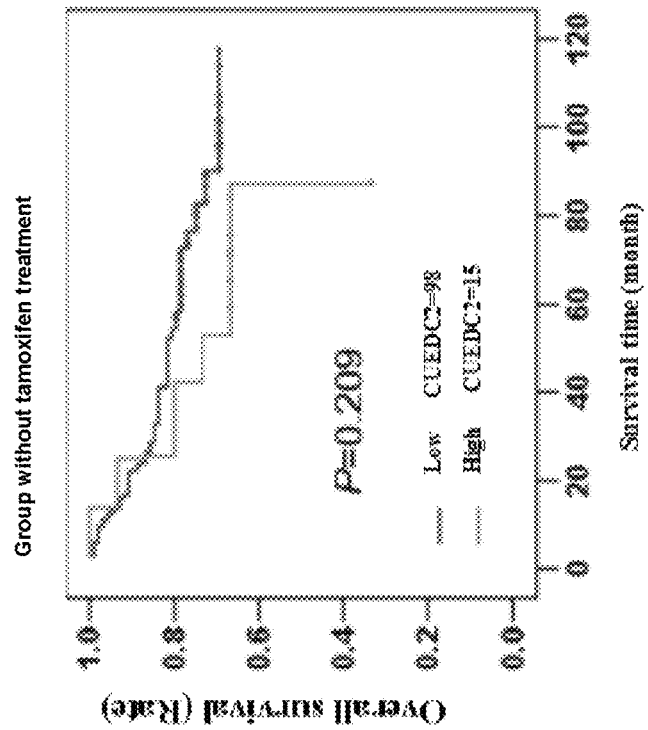
FIG. 11b shows overall survival curves of patients who did not receive tamoxifen, describing that, no matter the expression level of CUEDC2 is higher or lower, there is no statistical difference in disease-free survival rate and overall survival rate among these patients.
Figure 11A:
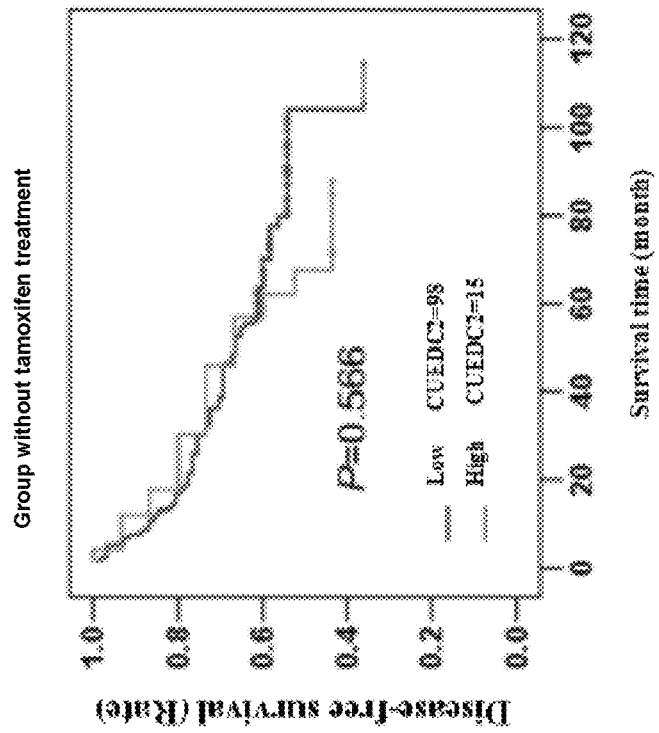
FIG. 11a shows survival curves of patients who did not receive tamoxifen.
Figure 12:
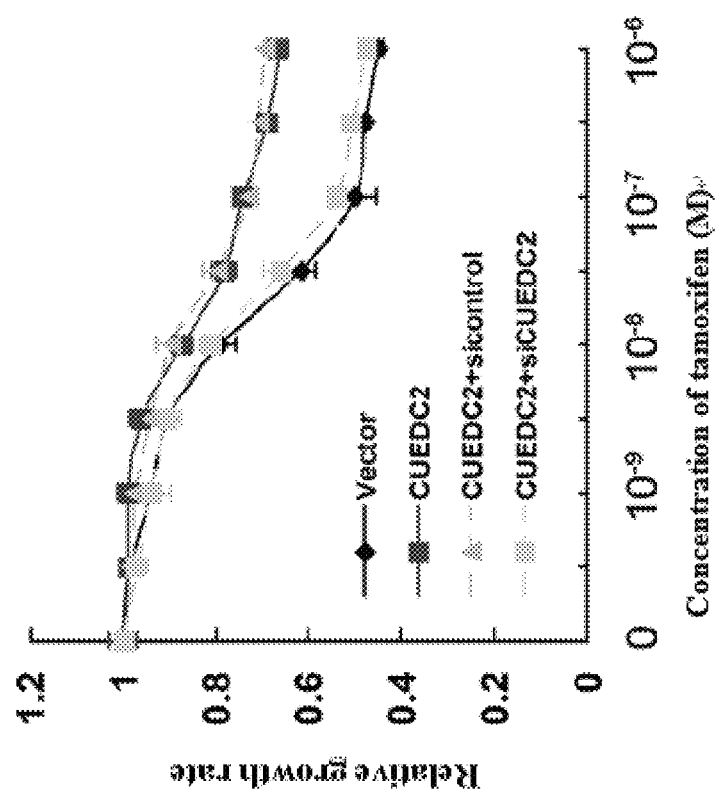
FIG. 12 shows MCF cell proliferation curves, describing that the sensitivity of cells to tamoxifen can be restored if MCF-7 cells with over expression of CUEDC2 are knocked down by CUEDC2 siRNA.
Figure 13:
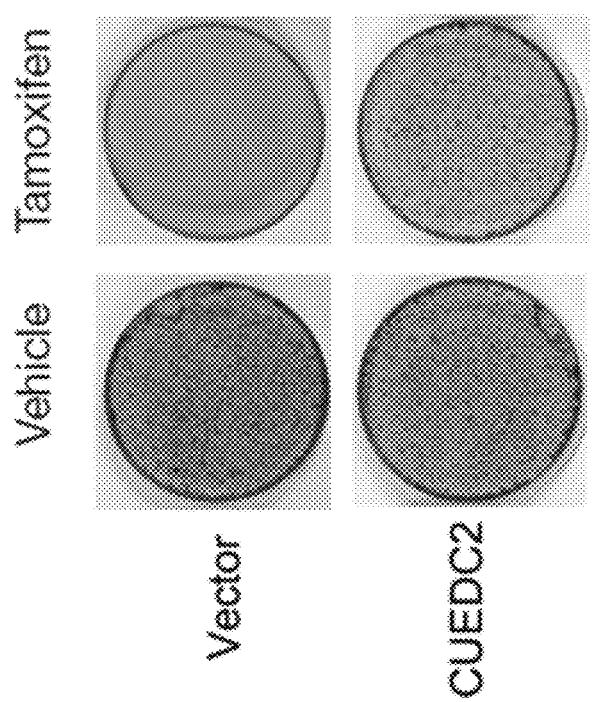
FIG. 13 is a crystal violet colony-formation graph, describing that the over expression of CUEDC2 significantly makes cells insensitive to cell death caused by tamoxifen.
Figure 14:
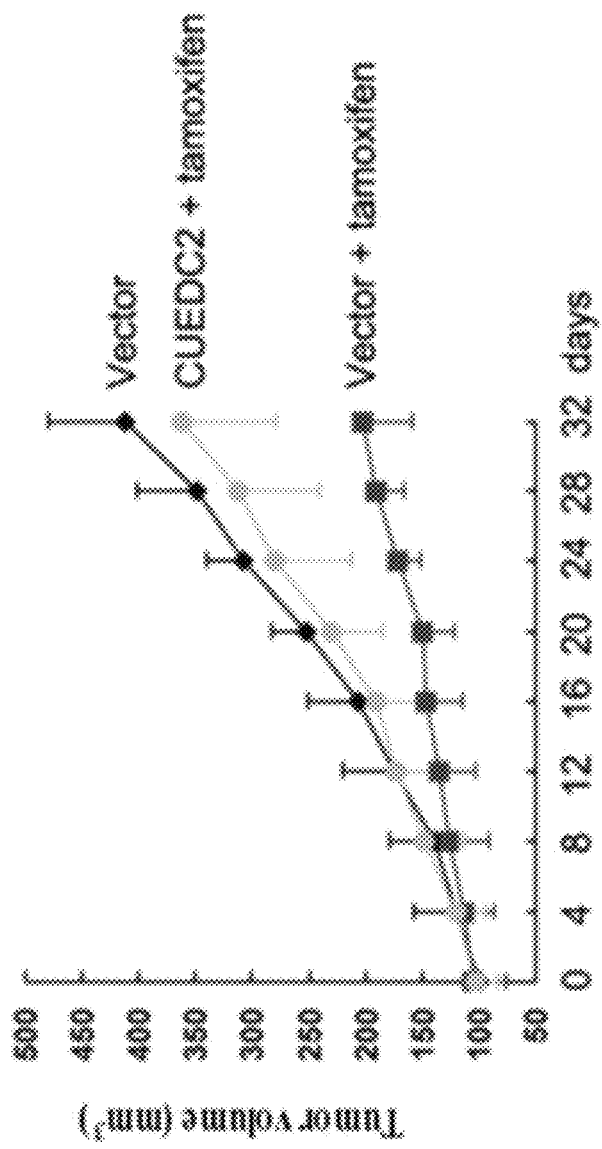
FIG. 14 shows experiments of tumor formation in nude mice, describing that tamoxifen cannot inhibit tumor growth effectively in nude mice xenografted with MCF-7 cells stably expressing CUEDC2.
Figure 15A:
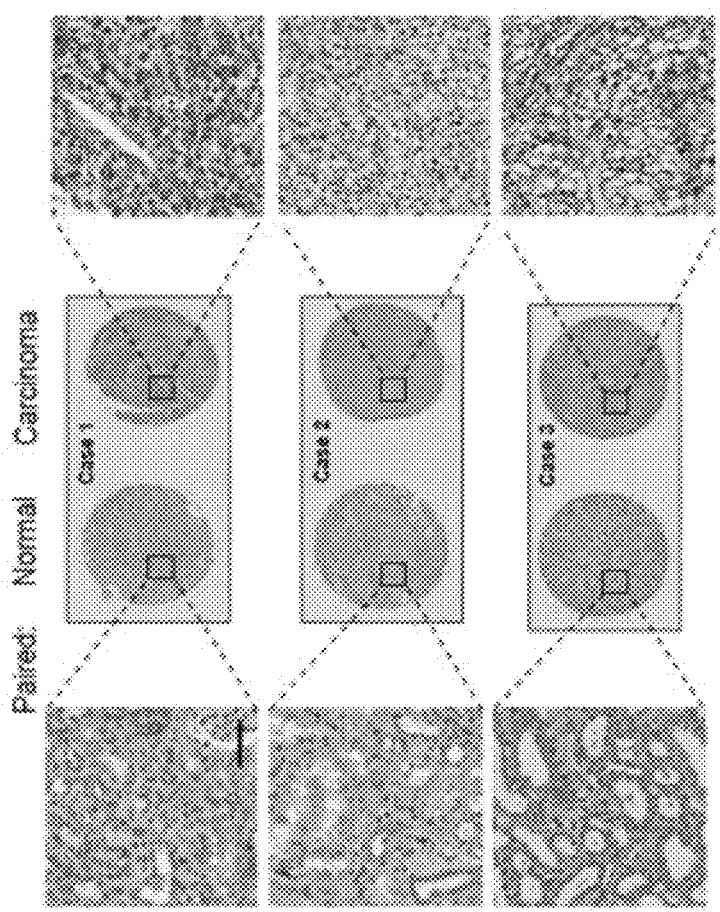
FIG. 15a shows three representative specimens of kidney tissue microarray, the left one is the normal tissue, and the right one is the kidney cancer tissue, the black boxes are magnified display areas, and the scale is 50 µm.
Figure 15B:
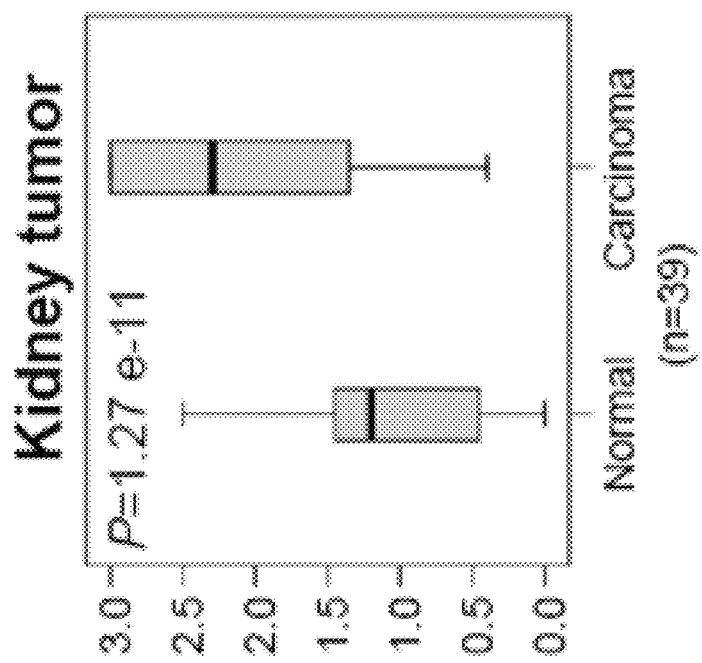
FIG. 15b is a boxplot graph showing the differences of expression levels of CUEDC2 in the normal kidney tissue and the kidney cancer tissue.
Figure 16A:
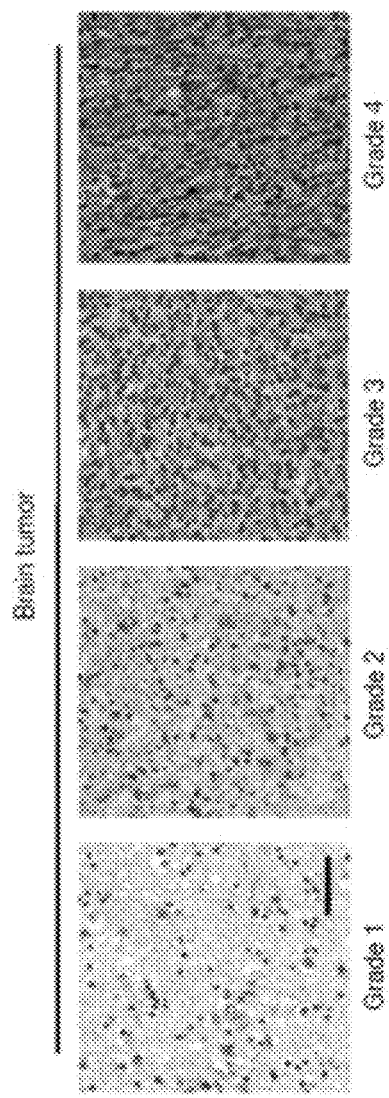
FIG. 16a shows representative images of immunohistochemical staining for CUEDC2 in brain tumor with different histological grades, the left ones are images with lower grades, the right ones are images with higher grades, and the scale is 50 µm.
Figure 16B:
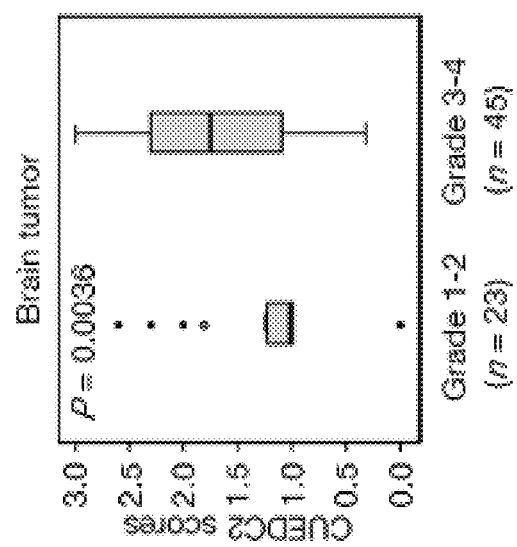
FIG. 16b is a box plot of CUEDC2 expression in brain tumor with different histological grades.
Figure 17:
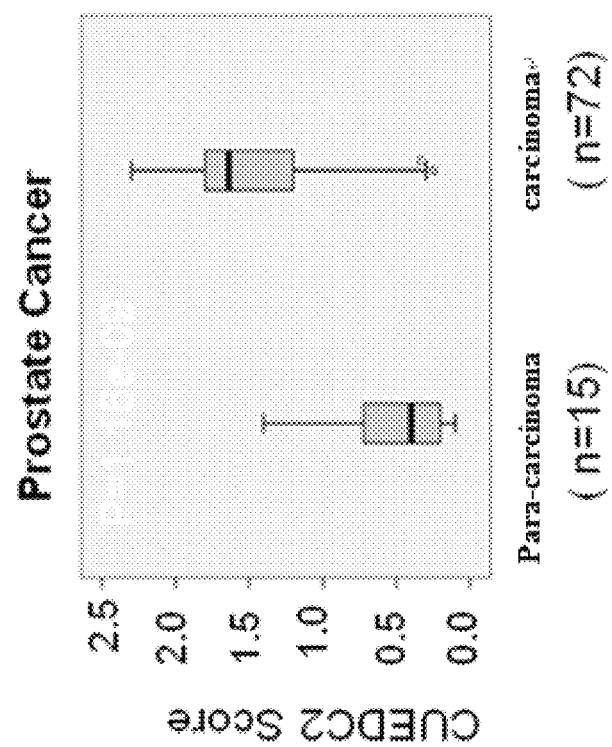
FIG. 17 is a boxplot graph showing differences of expression levels of CUEDC2 in normal tissues and in prostate cancer tissues.
Figure 18:
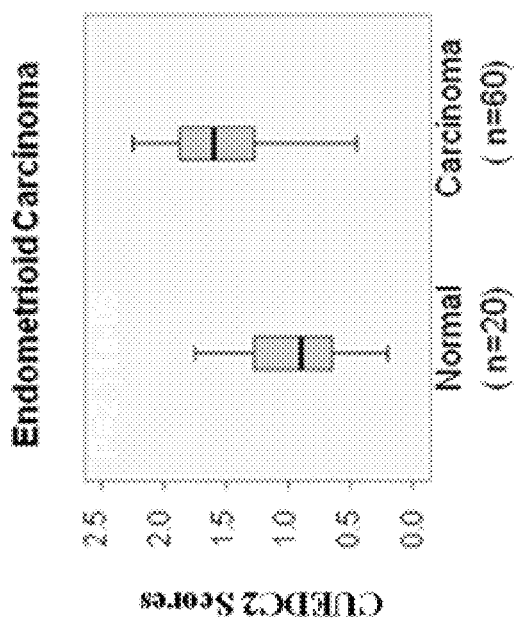
FIG. 18 is a boxplot graph showing differences of expression levels of CUEDC2 in normal tissues and in endometrial adenocarcinoma tissues.
Figure 19A:
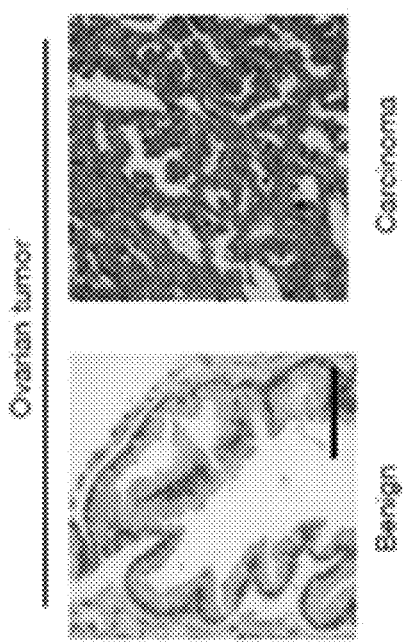
FIG. 19(a) shows representative images of immunohistochemical staining for CUEDC2 in ovarian tumor and benign tissue. The left one shows benign ovarian tumor tissue, the right one shows ovarian cancer tissue, and the scale is 50 µm.
Figure 19B:
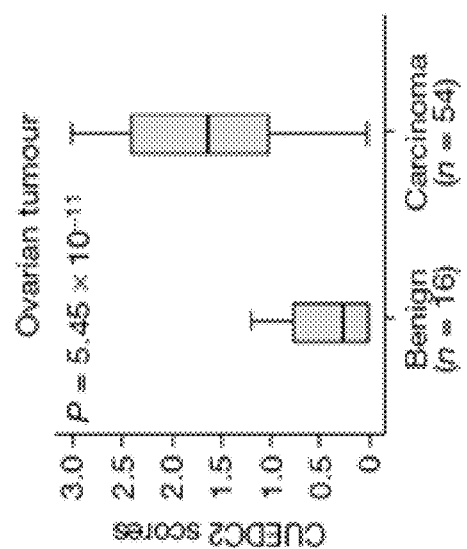
FIG. 19(b) is a boxplot graph showing differences of expression levels of CUEDC2 in benign ovarian tissue and in ovarian cancer tissue. Tissue microarrays were stained with CUEDC2 specific antibody, and the sample sizes of the two groups for statistical analysis were n=16 and n=54. There were significant differences in statistical analysis, $P<0.01$, t test.

II. The method and result:

The immunohistochemical method was the same as that in the embodiment 2, and the scoring standards of CUEDC2, ERα, PR, EGRF (HER-1), ERBB2 (HER-2/Neu) and Ki-67 were also the same as those in the embodiment 2. First, the Spearman correlation analysis was made on the correlation between the CUEDC2 expression level and expression levels of ERα, PR, EGFR (HER-1), ERBB2 (HER-2/Neu) and Ki-67. The result showed that CUEDC2 expression was negatively correlated with ERα and PR expression and positively correlated with expression of Ki-67 and HER-2 expression, whereas no statistical correlation between CUEDC2 expression level and HER-1 expression level (Table 1). The further analysis on the correlation between the CUEDC2 expression level and expression levels of ERα and PR in breast cancer patients showed that patients having higher CUEDC2 expression levels had lower expression levels and lower positive rates of ERα and PR (FIG. 8). In different histological grades of breast cancer patients, the higher the histological grade, the higher the CUEDC2 expression level. At the same time, the ERα expression level was decreased along with the increase of the tumor grades (FIG. 9a and FIG. 9b). The result above showed that, CUEDC2 expression has an inverse correlation with ER-α in breast cancers.

Embodiment 4: Breast Cancer Patients with Higher CUEDC2 Expression Levels Were Less Sensitive to Tamoxifen Therapy.

I. The Method:

The inventors did a survival analysis to 228 breast cancer patients with follow-up data. Disease-free survival (DFS) and overall survival (OS) were respectively defined as the time of illness from diagnosis to the first recurrence or death of breast cancer, the survival time of patients who were still alive at the last time follow-up was ended on the follow-up date, and the survival time of patients who died of non breast cancer diseases was ended on the death time. The survival curves were drawn by the Kaplan-Meier method, and the survival curves were statistically analyzed by the log rank test. In all statistical analysis, P values less than 0.05 (P<0.05) were considered statistically significant. The statistical analysis was completed with software SPSS 13.0.

II. The Result:

In order to evaluate the clinical significance of down-regulating ERα by CUEDC2, the inventor performed a survival analysis to 228 breast cancer patients with follow-up data. 115 of these patients received tamoxifen therapy, and for these 115 patients, both disease-free survival (DFS) and overall survival (OS) of patients with higher CUEDC2 expression levels were lower than those of patients with lower CUEDC2 expression levels. While the other 113 patients did not receive tamoxifen therapy, and for these 113 patients, no matter CUEDC2 expression level is higher or lower, neither disease-free survival nor overall survival had any statistical differences. The results above showed that breast cancer patients with higher CUEDC2 expression levels had lower sensitivity to tamoxifen therapy than patients with lower CUEDC2 expression levels, suggesting that CUEDC2 may play a potentially important role in making patients resistant to drugs in endocrinology therapy for breast cancer.

Embodiment 5: Over Expression of CUEDC2 Made Breast Cancer Cells Insensitivity to Tamoxifen.

I. The Material:

4-week-old female nude mice were purchased from Animal Laboratory Center of the Academy of Military Medical Sciences; the Cell Titer Glo Luminescent Cell Viability Assay was purchased from Promega Company; the Estrogen and tamoxifen sustained-release tablets were purchased from Innovative Research of America.

II. The Method and Result:

MCF-7 cells stably transfected with CUEDC2 were treated with different doses of tamoxifen, and then the cell growth was observed by a cell counting method. The results showed that, over expression of CUEDC2 really caused MCF-7 cells insensitive to tamoxifen. In order to eliminate nonspecific effects of over expression of CUEDC2 on cells growth, the inventors knocked down the CUEDC2 expression in the cells and did the same cell growth experiment. The result showed that, interference of CUEDC2 restored the sensitivity of MCF-7/CUEDC2 to tamoxifen. In addition, the inventors did the crystal violet clony-formation assay, and found that over expression of CUEDC2 noticeably made cells insensitive to tamoxifen-induced cell death, while the control MCF-7 empty vector cells were sensitive. In order to verify the above conclusion, the inventors further conducted animal experiments. $5 \times 10^6$ MCF-7/vector or MCF-7/CUEDC2 cells were injected into the mammary fat pad of ovariectomized nude mice, and estrogen sustained-release tablets were embedded subcutaneously. When tumors grew to 100-150 $mm^3$, nude mice were divided into two groups randomly, and embedded with tamoxifen or control placebo pills subcutaneously. Through continuous observation and tumor size measurement, the inventors found that tamoxifen could significantly inhibit the tumor growth of MCF-7/vector cells in nude mice, but could not inhibit tumor growth of MCF-7/CUEDC2 cells. Therefore, all of the results showed that CUEDC2 can play an important role in making breast cancer cells resistant to tamoxifen.

What is claimed is:

1. A method for treating a human breast cancer patient, said method comprising:
   (a) contacting a breast cancer sample from the patient with a monoclonal antibody or a polyclonal antibody that binds specifically to CUE domain-containing 2 (CUEDC2) protein, thereby determining the expression level of the CUEDC2 protein in the sample;
   (b) comparing the CUEDC2 protein expression level determined in (a) to a given value, wherein a CUEDC2 protein in expression level lower than the given value indicates a higher sensitivity of the patient to tamoxifen, and a CUEDC2 protein expression level equal to or higher than the given value indicates a lower sensitivity of the patient to tamoxifen, and
   (c) administering tamoxifen to the patient indicated in (b) as having a higher sensitivity to tamoxifen.

2. A method of determining the outcome of a human subject having breast cancer treated with tamoxifen, said method comprising:
   (a) administering tamoxifen to the subject;
   (b) obtaining a breast cancer sample from said subject following the administration of (a);
   (c) contacting said breast cancer sample from said subject with a monoclonal antibody or a polyclonal antibody that binds specifically to CUE domain-containing 2 (CUEDC2) protein, thereby determining the expression level of the CUEDC2 protein in the sample; and
   (d) comparing the CUEDC2 protein expression level determined in (c) to a given value wherein a CUEDC2 protein expression level lower than the given value indicates a better prognosis, and a CUEDC2 protein expression level equal to or higher than the given value indicates a worse prognosis.

* * * * *